United States Patent
Gutsche et al.

(10) Patent No.: US 9,332,756 B2
(45) Date of Patent: May 10, 2016

(54) LIQUID FORMULATIONS OF CARBOXAMIDE ARTHROPODICIDES

(75) Inventors: Oliver Walter Gutsche, Wilmington, DE (US); Isaac Billy Annan, Newark, DE (US); Hector Eduardo Portillo, Bear, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 1243 days.

(21) Appl. No.: 12/159,124

(22) PCT Filed: Dec. 27, 2006

(86) PCT No.: PCT/US2006/049315
§ 371 (c)(1),
(2), (4) Date: Jun. 25, 2008

(87) PCT Pub. No.: WO2007/081553
PCT Pub. Date: Jul. 19, 2007

(65) Prior Publication Data
US 2008/0305093 A1    Dec. 11, 2008

Related U.S. Application Data

(60) Provisional application No. 60/756,377, filed on Jan. 5, 2006, provisional application No. 60/855,606, filed on Oct. 31, 2006, provisional application No. 60/858,296, filed on Nov. 10, 2006.

(51) Int. Cl.
*A01N 43/56* (2006.01)
*A01N 63/00* (2006.01)

(52) U.S. Cl.
CPC ............... *A01N 43/56* (2013.01); *A01N 63/00* (2013.01)

(58) Field of Classification Search
None
See application file for complete search history.

(56) References Cited

U.S. PATENT DOCUMENTS

| | | | |
|---|---|---|---|
| 5,093,124 A * | 3/1992 | Kulenkampff | 424/406 |
| 5,393,791 A * | 2/1995 | Roberts | 514/762 |
| 6,603,044 B1 | 8/2003 | Tohnishi et al. | |
| 6,747,047 B2 | 6/2004 | Lahm et al. | |
| 7,232,836 B2 | 6/2007 | Lahm et al. | |
| 7,247,647 B2 | 7/2007 | Hughes et al. | |
| 7,696,232 B2 | 4/2010 | Berger et al. | |
| 7,696,233 B2 | 4/2010 | Lahm et al. | |
| 7,875,634 B2 | 1/2011 | Hughes et al. | |
| 7,902,231 B2 | 3/2011 | Lahm et al. | |
| 8,475,819 B2 | 7/2013 | Hughes et al. | |
| 8,530,382 B2 | 9/2013 | Tam | |
| 2008/0027046 A1 | 1/2008 | Annan et al. | |
| 2009/0075819 A1 * | 3/2009 | Kordes et al. | 504/100 |
| 2009/0104145 A1 | 4/2009 | Hughes et al. | |
| 2010/0055084 A1 | 3/2010 | Gutsche et al. | |
| 2010/0137374 A1 | 6/2010 | Annan et al. | |
| 2011/0059846 A1 | 3/2011 | Gutsche et al. | |
| 2012/0156262 A1 | 6/2012 | Gutsche et al. | |
| 2013/0028879 A1 | 1/2013 | Lahm et al. | |
| 2013/0031677 A1 | 1/2013 | Berger et al. | |
| 2013/0189228 A1 | 7/2013 | Hughes et al. | |

FOREIGN PATENT DOCUMENTS

| | | | |
|---|---|---|---|
| EP | 0149459 | 7/1985 | |
| WO | WO 98/28269 | 7/1998 | |
| WO | WO 98/57937 | 12/1998 | |
| WO | WO 02/063956 | 8/2002 | |
| WO | WO 03/015519 A1 | 2/2003 | |
| WO | WO 2004/067528 * | 8/2004 | C07D 401/04 |
| WO | WO 2006/068669 | 6/2006 | |

OTHER PUBLICATIONS

Office Actions mailed Jun. 23, 2010, Dec. 6, 2010; and Jun. 30, 211, in co-pending U.S. Appl. No. 11/628,145.

* cited by examiner

*Primary Examiner* — Alicia L Otton
(74) *Attorney, Agent, or Firm* — Linda D. Birch

(57) ABSTRACT

Disclosed are suspension concentrate compositions comprising by weight based on the total weight of the composition, about 0.1 to about 40% of at least one carboxamide arthropodicide; 0 to about 20% of at least one other biologically active agent; about 30 to about 95% of at least one water-immiscible liquid carrier; about 2 to about 50% of at least one emulsifier; about 0.01 to about 10% of a silica thickener; about 0.1 to about 10% of at least one protic solvent selected from water, a $C_1$-$C_{12}$ alkanol and a $C_2$-$C_3$ glycol; and about 0.001 to about 5% of at least one water-soluble carboxylic acid. A method for controlling an arthropod pest comprising diluting said suspension concentrate composition with water, and optionally adding an adjuvant to form a diluted composition, and contacting the arthropod pest or its environment with an effective amount of said diluted composition is also disclosed.

5 Claims, No Drawings

LIQUID FORMULATIONS OF CARBOXAMIDE ARTHROPODICIDES

This application is a 371 national stage entry of PCT/US2006/049315, internationally filed on Dec. 27, 2006. PCT/US2006/049315 claims priority from Provisional Application No. 60/756,377, filed on Jan. 5, 2006, from Provisional Application No. 60/855,606, filed on Oct. 31, 2006, and from Provisional Application No. 60/858,296, filed on Nov. 10, 2006.

FIELD OF THE INVENTION

This invention relates to certain suspension concentrate compositions comprising carboxamide arthropodicides, a method for producing the compositions, and the use of the compositions of the invention for controlling arthropods.

BACKGROUND OF THE INVENTION

Anthranilamides (see U.S. Pat. No. 6,747,047, PCT Publications WO 2003/015519 and WO 2004/067528) and phthalic diamides (see U.S. Pat. No. 6,603,044) are recently discovered classes of carboxamide arthropodicides having activity against numerous arthropod pests of economic importance.

Carboxamide arthropodicides like other agricultural chemicals can be formulated as concentrates in a variety of different forms, including liquid compositions such as suspension concentrates and solid compositions such as wettable powders and granules.

Typically chemical compounds for protecting plants, e.g., arthropodicides, are formulated as compositions (formulations) comprising the active compound(s) and inert ingredients such as carriers and adjuvants. These compositions can be applied by the user to the target plants/pests undiluted or after dilution with water. Liquid formulation concentrates are among the most commonly used formulations for plant protection chemicals, because they can be easily measured and poured, and when diluted with water typically form easily sprayed aqueous solutions or dispersions.

Because the efficacy and chemical stability of the active ingredient and physical stability of the formulated composition may be affected by inert ingredients in the formulation, suitable inert ingredients should not cause decomposition of the active ingredient, substantially diminish its activity on application, or cause appreciable precipitation or crystal formation upon long-term storage. Furthermore, inert ingredients should be nonphytotoxic and environmentally safe. Inert ingredients of formulations intended for dilution with water before application should be easily dissolved or dispersed in water. In certain formulations inert ingredients (often termed adjuvants) can even enhance the biological performance of the active ingredient by facilitating penetration or uptake into the plant or arthropod pest or by increasing resistance to wash-off. While such adjuvant properties are not essential, they are highly desirable.

Novel liquid suspension concentrate formulations comprising solid carboxamide arthropodicides having superior properties have now been discovered.

SUMMARY OF THE INVENTION

This invention is directed to an arthropodicidal suspension concentrate composition comprising by weight based on the total weight of the composition:

(a) about 0.1 to about 40% of at least one carboxamide arthropodicide that is solid at room temperature;
(b) 0 to about 20% of at least one other biologically active agent;
(c) about 30 to about 95% of at least one water-immiscible liquid carrier;
(d) about 0 to about 50% of at least one emulsifier;
(e) about 0.01 to about 10% of a silica thickener;
(f) about 0.1 to about 10% of at least one protic solvent selected from water, a $C_1$-$C_{12}$ alkanol and a $C_2$-$C_3$ glycol; and
(g) about 0.001 to about 5% of at least one water-soluble carboxylic acid.

This invention also relates to a method for controlling an arthropod pest comprising diluting said suspension concentrate composition with water and optionally adding an adjuvant to form a diluted composition, and contacting the arthropod pest or its environment with an effective amount of said diluted composition.

DETAILS OF THE INVENTION

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "suspension concentrate composition" and derivative terms such as "an arthropodicidal suspension concentrate composition" refer to compositions comprising finely divided solid particles of an active ingredient dispersed in water or organic liquid. Said particles retain identity and can be physically separated from liquid.

Embodiments of the present invention include:

Embodiment 1

The arthropodicidal suspension concentrate composition described in the Summary of the Invention wherein component (a) (i.e. the at least one carboxamide arthropodicide) is selected from anthranilamides (also described as anthranilic diamides) of Formula 1, N-oxides, and salts thereof

1

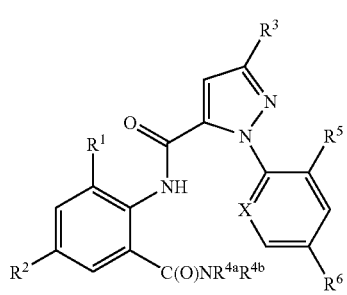

wherein
X is N, CF, CCl, CBr or CI;
$R^1$ is $CH_3$, Cl, Br or F;
$R^2$ is H, F, Cl, Br or —CN;
$R^3$ is F, Cl, Br, $C_1$-$C_4$ haloalkyl or $C_1$-$C_4$ haloalkoxy;
$R^{4a}$ is H, $C_1$-$C_4$ alkyl, cyclopropylmethyl or 1-cyclopropylethyl;
$R^{4b}$ is H or $CH_3$;
$R^5$ is H, F, Cl or Br; and
$R^6$ is H, F, Cl or Br.

Embodiment 1A

The composition of Embodiment 1 wherein X is N; $R^1$ is $CH_3$; $R^2$ is Cl or —CN; $R^3$ is Cl, Br or $CF_3$; $R^{4a}$ is $C_1$-$C_4$ alkyl; $R^{4b}$ is H; $R^5$ is Cl; and $R^6$ is H.

Embodiment 1B

The composition of Embodiment 1 wherein X is N; $R^1$ is $CH_3$; $R^2$ is Cl or —CN; $R^3$ is Cl, Br or $CF_3$; $R^{4a}$ is Me or $CH(CH_3)_2$; $R^{4b}$ is H; $R^5$ is Cl; and $R^6$ is H.

Embodiment 1C

The composition of Embodiment 1 wherein the at least one carboxamide arthropodicide is selected from
N-[4-chloro-2-methyl-6-[[(1-methylethyl)amino]carbonyl]phenyl]-1-(3-chloro-2-pyridinyl)-3-(trifluoromethyl)-1H-pyrazole-5-carboxamide,
N-[4-chloro-2-methyl-6-[(methylamino)carbonyl]phenyl]-1-(3-chloro-2-pyridinyl)-3-(trifluoromethyl)-1H-pyrazole-5-carboxamide,
3-bromo-N-[4-chloro-2-methyl-6-[[(1-methylethyl)amino]carbonyl]phenyl]-1-(3-chloro-2-pyridinyl)-1H-pyrazole-5-carboxamide,
3-bromo-N-[4-chloro-2-methyl-6-[(methylamino)carbonyl]phenyl]-1-(3-chloro-2-pyridinyl)-1H-pyrazole-5-carboxamide,
3-bromo-1-(3-chloro-2-pyridinyl)-N-[4-cyano-2-methyl-6-[(methylamino)-carbonyl]phenyl]-1H-pyrazole-5-carboxamide,
1-(3-chloro-2-pyridinyl)-N-[4-cyano-2-methyl-6-[(methylamino)carbonyl]-phenyl]-3-(trifluoromethyl)-1H-pyrazole-5-carboxamide,
3-bromo-1-(2-chlorophenyl)-N-[4-cyano-2-methyl-6-[[(1-methylethyl)-amino]carbonyl]phenyl]-1H-pyrazole-5-carboxamide,
3-bromo-1-(2-chlorophenyl)-N-[4-cyano-2-methyl-6-[(methylamino)-carbonyl]phenyl]-1H-pyrazole-5-carboxamide,
3-bromo-1-(2-chlorophenyl)-N-[2,4-dichloro-6-[(methylamino)carbonyl]-phenyl]-1H-pyrazole-5-carboxamide,
3-bromo-N-[4-chloro-2-[[(cyclopropylmethyl)amino]carbonyl]-6-methylphenyl]-1-(3-chloro-2-pyridinyl)-1H-pyrazole-5-carboxamide,
3-bromo-1-(3-chloro-2-pyridinyl)-N-[4-cyano-2-[[(cyclopropylmethyl)-amino]-carbonyl]-6-methylphenyl]-1H-pyrazole-5-carboxamide,
3-bromo-N-[4-chloro-2-[[(1-cyclopropylethyl)amino]carbonyl]-6-methylphenyl]-1-(3-chloro-2-pyridinyl)-1H-pyrazole-5-carboxamide, and
3-bromo-1-(3-chloro-2-pyridinyl)-N-[4-cyano-2-[[(1-cyclopropylethyl)-amino]carbonyl]-6-methylphenyl]-1H-pyrazole-5-carboxamide.

Embodiment 2

The arthropodicidal suspension concentrate composition described in the Summary of the Invention wherein component (a) (i.e. the at least one carboxamide arthropodicide) is selected from phthalic diamides of Formula 2 and salts thereof

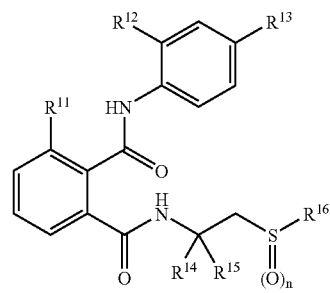

wherein
$R^{11}$ is $CH_3$, Cl, Br or I;
$R^{12}$ is $CH_3$ or Cl;
$R^{13}$ is $C_1$-$C_3$ fluoroalkyl;
$R^{14}$ is H or $CH_3$;
$R^{15}$ is H or $CH_3$;
$R^{16}$ is $C_1$-$C_2$ alkyl; and
n is 0, 1 or 2.

Embodiment 2A

The composition of Embodiment 2 wherein $R^{11}$ is Cl, Br or I; $R^{12}$ is $CH_3$; $R^{13}$ is $CF_3$, $CF_2CF_3$ or $CF(CF_3)_2$ (equivalently identified as $(CF_3)_2CF$); $R^{14}$ is H or $CH_3$; $R^{15}$ is H or $CH_3$; $R^{16}$ is $CH_3$; and n is 0, 1 or 2.

Embodiment 2B

The composition of Embodiment 2 wherein the at least one carboxamide arthropodicide is $N^2$-[1,1-dimethyl-2-(methylsulfonyl)ethyl]-3-iodo-$N^1$-[2-methyl-4-[1,2,2,2-tetrafluoro-1-(trifluoromethyl)ethyl]phenyl]-1,2-benzenedicarboxamide.

Embodiment 3

The arthropodicidal suspension concentrate composition described in the Summary of the Invention wherein component (a) (i.e. the at least one carboxamide arthropodicide) is from about 5 to about 25% of the composition by weight.

Embodiment 3A

The arthropodicidal suspension concentrate composition of Embodiment 3 wherein component (a) is from about 5 to about 15% of the composition by weight of the composition.

Embodiment 4

The composition described in the Summary of the Invention wherein component (a) (i.e. the at least one carboxamide arthropodicide) comprises a carboxamide arthropodicide having a melting point above about 80° C.

Embodiment 4A

The composition of Embodiment 4 wherein component (a) comprises a carboxamide arthropodicide having a melting point above about 100° C.

Embodiment 4B

The composition of Embodiment 4A wherein component (a) comprises a carboxamide arthropodicide having a melting point above about 120° C.

Embodiment 5

The arthropodicidal suspension concentrate composition described in the Summary of the Invention wherein component (b) (i.e. the at least one other biologically active agent) is selected from insecticides, nematocides, bactericides, acaricides, molluscides, fungicides, herbicides, safeners, plant growth regulators and plant nutrients.

Embodiment 5A

The arthropodicidal suspension concentrate composition of Embodiment 5 wherein component (b) is selected from abamectin, acetamiprid, amitraz, avermectin, azadirachtin, bifenthrin, buprofezin, cartap, chlorfenapyr, chlorpyrifos, clothianidin, cyfluthrin, beta-cyfluthrin, cyhalothrin, lambda-cyhalothrin, cypermethrin, cyromazine, deltamethrin, dieldrin, dinotefuran, diofenolan, emamectin, endosulfan, esfenvalerate, ethiprole, fenothiocarb, fenoxycarb, fenvalerate, fipronil, flonicamid, flufenoxuron, hexaflumuron, hydramethylnon, imidacloprid, indoxacarb, lufenuron, metaflumizone, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, tebufenozide, thiacloprid, thiamethoxam, thiodicarb, thiosultap-sodium, tralomethrin, triazamate, triflumuron, *Bacillus thuringiensis* subsp. *aizawai*, *Bacillus thuringiensis* subsp. *kurstaki*, nucleopolyhedrovirus (NPV), and an encapsulated delta-endotoxin of *Bacillus thuringiensis*.

Embodiment 5B

The arthropodicidal suspension concentrate composition described in the Summary of the Invention wherein component (b) (i.e. the at least one other biologically active agent) is from 0 to about 15% of the composition by weight.

Embodiment 6

The arthropodicidal suspension concentrate composition described in the Summary of the Invention wherein component (c) (i.e. the at least one water-immiscible liquid carrier) is from about 30 to about 80% of the composition by weight.

Embodiment 6A

The arthropodicidal suspension concentrate composition of Embodiment 6 wherein component (c) is from about 40 to about 70% of the composition by weight.

Embodiment 6B

The arthropodicidal suspension concentrate composition of Embodiment 6A wherein component (c) is from about 50 to about 60% of the composition by weight.

Embodiment 6C

The arthropodicidal suspension concentrate composition described in the Summary of the Invention wherein component (c) (i.e. the at least one water-immiscible liquid carrier) comprises at least one substance selected from the group consisting of fatty acid esters of a $C_1$-$C_4$ alkanols (including those derived from seed and fruit oils), alkoxylated fatty acid esters (including those derived from seed and fruit oils), vegetable oils and mineral oils.

Embodiment 6D

The arthropodicidal suspension concentrate composition of Embodiment 6C wherein component (c) comprises a fatty acid ester of a $C_1$-$C_4$ alkanol.

Embodiment 6E

The arthropodicidal suspension concentrate composition of Embodiment 6D wherein component (c) comprises a saturated or an unsaturated $C_{10}$-$C_{22}$ fatty acid ester of a $C_1$-$C_4$ alkanol.

Embodiment 6F

The arthropodicidal suspension concentrate composition of Embodiment 6E wherein component (c) comprises a saturated or an unsaturated $C_{12}$-$C_{20}$ fatty acid ester of a $C_1$-$C_4$ alkanol.

Embodiment 6G

The arthropodicidal suspension concentrate composition of Embodiment 6F wherein component (c) comprises a saturated or an unsaturated $C_{16}$-$C_{18}$ fatty acid ester of a $C_1$-$C_4$ alkanol.

Embodiment 6H

The arthropodicidal suspension concentrate composition of Embodiment 6G wherein component (c) comprises a saturated or an unsaturated $C_{16}$-$C_{18}$ fatty acid ester of a $C_1$-$C_2$ alkanol.

Embodiment 6I

The arthropodicidal suspension concentrate composition of Embodiment 6H wherein component (c) comprises a saturated or an unsaturated $C_{16}$-$C_{18}$ fatty acid ester of methanol.

Embodiment 6J

The arthropodicidal suspension concentrate composition of Embodiment 6C wherein component (c) comprises a methylated seed oil of sunflower, soybean, cotton or linseed.

Embodiment 6K

The arthropodicidal suspension concentrate composition of Embodiment 6J wherein component (c) comprises methylated soybean oil (methyl soyate).

Embodiment 7

The arthropodicidal suspension concentrate composition described in the Summary of the Invention wherein component (d) (i.e. the at least one emulsifier) is from about 2 to about 50% of the composition by weight.

Embodiment 7A

The arthropodicidal suspension concentrate composition of Embodiment 7 wherein component (d) is from about 10 to about 40% of the composition by weight.

Embodiment 7B

The arthropodicidal suspension concentrate composition of Embodiment 7A wherein component (d) is from about 20 to about 30% of the composition by weight.

Embodiment 8

The arthropodicidal suspension concentrate composition described in the Summary of the Invention wherein component (d) (i.e. the at least one emulsifier) is selected from anionic surfactants, non-ionic surfactants, and mixtures thereof.

Embodiment 8A

The arthropodicidal suspension concentrate composition of Embodiment 8 wherein the anionic surfactants are selected from linear alkylbenzenesulfonates and branched alkylbenzenesulfonates.

Embodiment 8B

The arthropodicidal suspension concentrate composition of Embodiment 8 wherein component (d) comprises a linear alkylbenzenesulfonate anionic surfactant.

Embodiment 8C

The arthropodicidal suspension concentrate composition of Embodiment 8 wherein component (d) comprises a dodecylbenzenesulfonate anionic surfactant.

Embodiment 8D

The arthropodicidal suspension concentrate composition of Embodiment 8 wherein the non-ionic surfactants are selected from ethoxylated sorbitol esters, ethoxylated vegetable oils, and mixtures thereof.

Embodiment 8E

The arthropodicidal suspension concentrate composition of Embodiment 8 wherein the non-ionic surfactants are selected from ethoxylated sorbitol esters, ethoxylated sorbitan esters, ethoxylated fatty acid esters, and mixtures thereof.

Embodiment 8F

The arthropodicidal suspension composition of Embodiment 8 wherein component (d) comprises a non-ionic surfactant selected from an ethoxylated sorbitan trioleate, an ethoxylated sorbitol hexaoleate, an ethoxylated soybean oil, an ethoxylated castor oil, and a mixture thereof.

Embodiment 8G

The arthropodicidal suspension concentrate composition of Embodiment 8 wherein component (d) comprises a mixture of a dodecylbenzenesulfonate and an ethoxylated sorbitol hexaoleate.

Embodiment 8H

The arthropodicidal suspension concentrate composition of Embodiment 8 wherein component (d) comprises an ethoxylated castor oil.

Embodiment 8I

The arthropodicidal suspension composition of Embodiment 8 wherein component (d) comprises a mixture of an anionic surfactant and a non-ionic surfactant and the ratio of the anionic surfactant to the non-ionic surfactant ranges from about 2:1 to about 1:10 by weight.

Embodiment 8J

The arthropodicidal suspension concentrate composition of Embodiment 8 wherein component (d) comprises a mixture of an anionic surfactant and a non-ionic surfactant and the ratio of the anionic surfactant to the non-ionic surfactant ranges from about 2:1 to about 1:5 by weight.

Embodiment 8K

The arthropodicidal suspension concentrate composition described in the Summary of the Invention wherein component (d) (i.e. the at least one emulsifier) is in a ratio to component (c) (i.e. the at least one water-immiscible liquid carrier) of from about 1:1 to about 1:20 by weight.

Embodiment 9

The arthropodicidal suspension concentrate composition described in the Summary of the Invention wherein component (e) (i.e. the silica thickener) comprises fumed silica.

Embodiment 9A

The arthropodicidal suspension concentrate composition of Embodiment 9 wherein component (e) is from about 0.01 to about 5% of the composition by weight.

Embodiment 10

The arthropodicidal suspension concentrate composition described in the Summary of the Invention wherein component (f) (i.e. the at least one protic solvent) is from about 0.5 to about 5% of the composition by weight.

Embodiment 11

The arthropodicidal suspension concentrate composition described in the Summary of the Invention wherein component (f) (i.e. the at least one protic solvent) is selected from water, $C_1$-$C_4$ alkanols and ethylene glycol (including mixtures thereof).

Embodiment 11A

The arthropodicidal suspension concentrate composition of Embodiment 11 wherein component (f) is selected from water, methanol, ethanol and ethylene glycol (including mixtures thereof).

Embodiment 11B

The arthropodicidal suspension concentrate composition of Embodiment 11 wherein component (f) comprises water.

Embodiment 11C

The arthropodicidal suspension concentrate composition of Embodiment 11B wherein the water is from about 0.5 to about 5% of the composition by weight.

Embodiment 12

The arthropodicidal suspension concentrate composition described in the Summary of the Invention wherein component (g) (i.e. the at least one water-soluble carboxylic acid) is from about 0.01 to about 5% of the composition by weight.

Embodiment 12A

The arthropodicidal suspension concentrate composition of Embodiment 12 wherein component (g) is from about 0.01 to about 2% of the composition by weight.

Embodiment 13

The arthropodicidal suspension concentrate composition described in the Summary of the Invention wherein component (g) (i.e. the at least one water-soluble carboxylic acid) is selected from acetic acid, citric acid, propionic acid and mixtures thereof.

Embodiment 13A

The arthropodicidal suspension concentrate composition of Embodiment 13 wherein component (g) comprises citric acid.

Embodiment 13B

The arthropodicidal suspension concentrate composition of Embodiment 13A wherein the citric acid is from about 0.01 to about 2% of the composition by weight.

Of note as embodiments are methods for preparing the arthropodicidal suspension concentrate composition, and the use of said composition for controlling arthropods.

Embodiments of this invention, including Embodiments 1-13B above as well as any other embodiments described herein, pertain to the compositions and methods of the present invention, which can be combined in any manner.

Examples of combinations of Embodiments 1-13B include:

Embodiment A

The arthropodicidal suspension concentrate composition described in the Summary of the Invention wherein component (a) (i.e. the at least one carboxamide arthropodicide) is selected from anthranilamides of Formula 1, N-oxides, and salts thereof

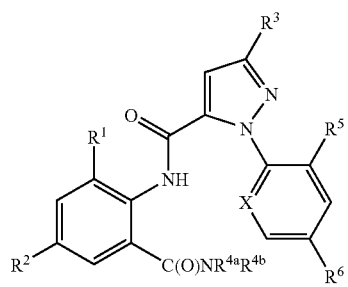

wherein
X is N, CF, CCl, CBr or CI;
$R^1$ is $CH_3$, Cl, Br or F;
$R^2$ is H, F, Cl, Br or —CN;
$R^3$ is F, Cl, Br, $C_1$-$C_4$ haloalkyl or $C_1$-$C_4$ haloalkoxy;
$R^{4a}$ is H, $C_1$-$C_4$ alkyl, cyclopropylmethyl or 1-cyclopropylethyl;
Rob is H or $CH_3$;
$R^5$ is H, F, Cl or Br; and
$R^6$ is H, F, Cl or Br.

Embodiment B

The arthropodicidal suspension concentrate composition described in the Summary of the Invention wherein component (a) (i.e. the at least one carboxamide arthropodicide) is selected from phthalic diamides of Formula 2 and salts thereof

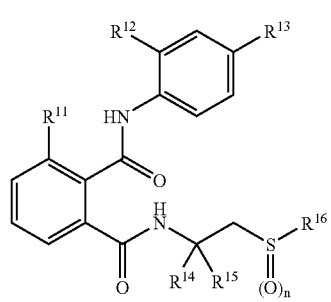

wherein
$R^{11}$ is $CH_3$, Cl, Br or I;
$R^{12}$ is $CH_3$ or Cl;
$R^{13}$ is $C_1$-$C_3$ fluoroalkyl;
$R^{14}$ is H or $CH_3$;
$R^{15}$ is H or $CH_3$;
$R^{16}$ is $C_1$-$C_2$ alkyl; and
n is 0, 1 or 2.

Embodiment C

The arthropodicidal suspension concentrate composition described in the Summary of the Invention or in Embodiment A or B wherein component (a) (i.e. the at least one carboxamide arthropodicide) is from about 5 to about 25% of the composition by weight; component (b) (i.e. the at least one other biologically active agent) is from 0 to about 15% of the composition by weight; component (c) (i.e. the at least one water-immiscible liquid carrier) comprises at least one substance selected from the group consisting of fatty acid esters of $C_1$-$C_4$ alkanols, alkoxylated fatty acid esters, vegetable oils and mineral oils, and is from about 40 to about 70% of the composition by weight; component (d) (i.e. the at least one emulsifier) is selected from anionic surfactants, non-ionic surfactants and mixtures thereof, and is from about 10 to about 40% of the composition by weight; component (e) (i.e. the silica thickener) is from about 0.01 to about 5% of the composition by weight; component (f) (i.e. the at least one protic solvent) is from about 0.5 to about 5% of the composition by weight; and component (g) (i.e. the at least one water-soluble carboxylic acid) is from about 0.01 to about 5% of the composition by weight.

Embodiment D

The arthropodicidal suspension concentrate composition of Embodiment C wherein component (c) comprises a saturated or an unsaturated $C_{16}$-$C_{18}$ fatty acid ester of a $C_1$-$C_2$ alkanol, and is from about 50 to about 60% of the composition by weight; component (d) comprises a mixture of an anionic surfactant and a non-ionic surfactant in a ratio of the anionic surfactant to the non-ionic surfactant ranging from about 2:1 to about 1:10; component (e) comprises fumed silica; component (f) comprises water, and the water is from about 0.5 to about 5% of the composition by weight; and component (g) comprises citric acid, and the citric acid is from about 0.01 to about 2% of the composition by weight.

Embodiment E

The arthropodicidal suspension concentrate composition of Embodiment C wherein component (c) comprises a methylated seed oil of sunflower, soybean, cotton or linseed.

Embodiment F

The arthropodicidal suspension concentrate composition of Embodiment E wherein component (c) comprises a methylated soybean oil (methyl soyate).

Embodiment G

The arthropodicidal suspension concentrate composition of Embodiment C wherein the anionic surfactant is a linear alkylbenzenesulfonate, the non-ionic surfactant is selected from ethoxylated sorbitol esters, ethoxylated sorbitan esters, ethoxylated fatty acid esters, and mixtures thereof, and the ratio of the anionic surfactant to the non-ionic surfactant ranges from about 2:1 to about 1:5 by weight.

Embodiment H

The arthropodicidal suspension concentrate composition of Embodiment G wherein component (d) comprises a mixture of a dodecylbenzenesulfonate and an ethoxylated sorbitol hexaoleate.

Of note are compositions of the present invention, including the Embodiments above, wherein component (b) (i.e. the at least one other biologically active agent) comprises other than spinetoram.

The term "carboxamide arthropodicide that is solid at room temperature" in the present context denotes an arthropodicidal compound useful for controlling arthropod pests, having one or more carboxamide moieties and a melting point higher than 20° C., or alternatively and typically higher than 50° C. More typically at least one carboxamide arthropodicide of component (a) has a melting point higher than about 80° C., even more typically above about 100° C., and most typically above about 120° C. Often all of the at least one carboxamide arthropodicides of component (a) have melting points higher than about 80° C., above about 100° C., or even above about 120° C. Typically the at least one carboxamide arthropodicide of component (a) have water solubility less than about 10 g/L and more typically less than about 5 g/L.

As is well known in the art, the term "carboxamide" refers to a moiety comprising a carbon, nitrogen and oxygen atom bonded in the configuration shown as Formula A. The carbon atom in Formula A is bonded to a carbon atom in a radical to which the carboxamide moiety is bonded. The nitrogen atom in Formula A is bonded to the carbonyl carbon of Formula A and also bonded to two other atoms, at least one atom of which is selected from a hydrogen atom or a carbon atom of another radical to which the carboxamide moiety is bonded.

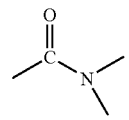

A

In one embodiment the present compositions comprise at least one carboxamide arthropodicide that is solid at room temperature and contains at least two carboxamide moieties. In another embodiment the at least one carboxamide arthropodicide contains at least two carboxamide moieties vicinally bonded to carbon atoms (i.e. in ortho arrangement) of a carbocyclic or heterocyclic ring. In a further embodiment the carbocyclic or heterocyclic ring of the at least one carboxamide arthropodicide is aromatic (i.e. satisfies the Hückel 4n+2 rule for aromaticity).

Of particular note as carboxamide arthropodicides useful in compositions of the present invention are those of Formula 1, N-oxides and salts thereof, and Formula 2 and salts thereof

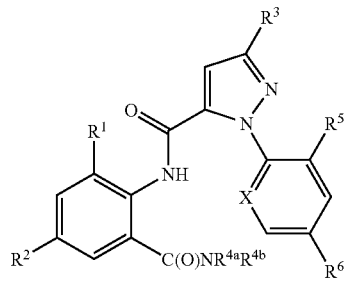

1 wherein
X is N, CF, CCl, CBr or CI;
R$^1$ is CH$_3$, Cl, Br or F;
R$^2$ is H, F, Cl, Br or —CN;
R$^3$ is F, Cl, Br, C$_1$-C$_4$ haloalkyl or C$_1$-C$_4$ haloalkoxy;
R$^{4a}$ is H, C$_1$-C$_4$ alkyl, cyclopropylmethyl or 1-cyclopropylethyl;
R$^{4b}$ is H or CH$_3$;
R$^5$ is H, F, Cl or Br; and
R$^6$ is H, F, Cl or Br;

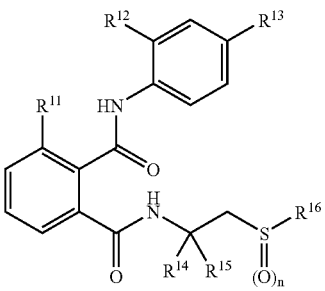

2 wherein
R$^{11}$ is CH$_3$, Cl, Br or I;
R$^{12}$ is CH$_3$ or Cl;
R$^{13}$ is C$_1$-C$_3$ fluoroalkyl;
R$^{14}$ is H or CH$_3$;
R$^{15}$ is H or CH$_3$;
R$^{16}$ is C$_1$-C$_2$ alkyl; and
n is 0, 1 or 2.

In the above recitations, the term "alkyl", used either alone or in compound words such as "haloalkyl" or "fluoroalkyl" includes straight-chain or branched alkyl, such as, methyl, ethyl, n-propyl, i-propyl, or the different butyl isomers. "Alkoxy" includes, for example, methoxy, ethoxy, n-propyloxy, isopropyloxy and the different butoxy isomers. The term "halogen", either alone or in compound words such as "haloalkyl", includes fluorine, chlorine, bromine or iodine. Further, when used in compound words such as "haloalkyl" or "haloalkoxy", said alkyl may be partially or fully substituted with halogen atoms which may be the same or different. Examples of "haloalkyl" include CF$_3$, CH$_2$Cl, CH$_2$CF$_3$ and CCl$_2$CF$_3$. The terms "haloalkoxy", and the like, are defined analogously to the term "haloalkyl". Examples of "haloalkoxy" include OCF$_3$, OCH$_2$Cl$_3$, OCH$_2$CH$_2$CHF$_2$ and OCH$_2$CF$_3$.

The total number of carbon atoms in a substituent group is indicated by the "C$_i$-C$_j$" prefix where i and j are numbers from 1 to 4. For example, C$_1$-C$_4$ alkyl designates methyl through butyl, including the various isomers.

Of particular note is the composition described in the Summary of the Invention wherein component (a) (i.e. the at least one carboxamide arthropodicide) comprises a carboxamide arthropodicides selected from the group consisting of
3-bromo-1-(3-chloro-2-pyridinyl)-N-[4-cyano-2-methyl-6-[(methylamino)carbonyl]-phenyl]-1H-pyrazole-5-carboxamide,
3-bromo-N-[4-chloro-2-methyl-6-[(methylamino)carbonyl]phenyl]-1-(3-chloro-2-pyridinyl)-1H-pyrazole-5-carboxamide,
N-[4-chloro-2-methyl-6-[[(1-methylethyl)amino]carbonyl]phenyl]-1-(3-chloro-2-pyridinyl)-3-(trifluoromethyl)-1H-pyrazole-5-carboxamide,
N-[4-chloro-2-methyl-6-[(methylamino)carbonyl]phenyl]-1-(3-chloro-2-pyridinyl)-3-(trifluoromethyl)-1H-pyrazole-5-carboxamide,
3-bromo-N-[4-chloro-2-methyl-6-[[(1-methylethyl)amino]carbonyl]phenyl]-1-(3-chloro-2-pyridinyl)-1H-pyrazole-5-carboxamide,
1-(3-chloro-2-pyridinyl)-N-[4-cyano-2-methyl-6-[(methylamino)carbonyl]phenyl]-3-(trifluoromethyl)-1H-pyrazole-5-carboxamide,
3-bromo-1-(2-chlorophenyl)-N-[4-cyano-2-methyl-6-[[(1-methylethyl)amino]-carbonyl]-phenyl]-1H-pyrazole-5-carboxamide,
3-bromo-1-(2-chlorophenyl)-N-[4-cyano-2-methyl-6-[(methylamino)carbonyl]phenyl]-1H-pyrazole-5-carboxamide,
3-bromo-1-(2-chlorophenyl)-N-[2,4-dichloro-6-[(methylamino)carbonyl]phenyl]-1H-pyrazole-5-carboxamide,
3-bromo-N-[4-chloro-2-[[(cyclopropylmethyl)amino]carbonyl]-6-methylphenyl]-1-(3-chloro-2-pyridinyl)-1H-pyrazole-5-carboxamide,
3-bromo-1-(3-chloro-2-pyridinyl)-N-[4-cyano-2-[[(cyclopropylmethyl)amino]-carbonyl]-6-methylphenyl]-1H-pyrazole-5-carboxamide,
3-bromo-N-[4-chloro-2-[[(1-cyclopropylethyl)amino]carbonyl]-6-methylphenyl]-1-(3-chloro-2-pyridinyl)-1H-pyrazole-5-carboxamide,
3-bromo-1-(3-chloro-2-pyridinyl)-N-[4-cyano-2-[[(1-cyclopropylethyl)amino]carbonyl]-6-methylphenyl]-1H-pyrazole-5-carboxamide, and
N$^2$-[1,1-dimethyl-2-(methylsulfonyl)ethyl]-3-iodo-N$^1$-[2-methyl-4-[1,2,2,2-tetrafluoro-1-(trifluoromethyl)ethyl]phenyl]-1,2-benzenedicarboxamide.

The carboxamide arthropodicides (e.g., Formula 1) for the present compositions can also be in the form of N-oxides. One skilled in the art will appreciate that not all nitrogen-containing heterocyclic rings can form N-oxides since the nitrogen requires an available lone pair for oxidation to the oxide; one skilled in the art will recognize those nitrogen-containing heterocyclic rings which can form N-oxides. One skilled in the art will also recognize that tertiary amines can form N-oxides. Synthetic methods for the preparation of N-oxides of heterocyclic rings and tertiary amines are very well known by one skilled in the art including the oxidation of heterocyclic rings and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding non-salt forms, salts share the biological utility of the nonsalt forms. Thus a wide variety of salts of carboxamide arthropodicides (e.g., Formulae 1 or 2) are useful in the present compositions (i.e. are agriculturally suitable). Such salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. Salts can also include those formed with organic bases (e.g., pyridine, triethylamine or ammonia) or inorganic bases (e.g., hydrides, hydroxides or carbonates of sodium, potassium, lithium, calcium, magnesium or barium) when the carboxamide arthropodicide contains an acidic moiety such as a carboxylic acid or phenol.

The composition of the invention generally comprises component (a) (i.e. the at least one carboxamide arthropodicide) in an amount typically from about 0.1 to about 40%, more typically from about 5 to about 25%, and most typically from about 5 to about 15% of the composition by weight.

The compositions of the present invention can comprise in addition to the at least one carboxamide arthropodicide up to about 20%, or up to about 15% by weight of component (b) (i.e. the at least one other biologically active agent). The at least one other biologically active agent is a compound that differs from the at least one carboxamide arthropodicide and can include a compound, agent or substance selected from the following classes: insecticides, fungicides, nematocides, bactericides, acaricides, herbicides, growth regulators such as rooting stimulants, chemosterilants, semiochemicals, repellents, attractants, pheromones, feeding stimulants, including both chemical and biological agents, and mixtures of several compounds, agents or substances selected from the above classes. In one embodiment the at least one other biologically active agent is solid at room temperature, and in another embodiment the at least one other biologically active agent has a melting point higher than 50° C.

Mixtures of different biologically active agents can have a broader spectrum of activity than a single agent alone. Furthermore, such mixtures can exhibit a synergistic effect. In an embodiment of the present invention, the arthropodicidal suspension concentrate composition further comprises at least one other biologically active agent wherein the other biologically active agent is suspended or dissolved in the at least one water-immiscible liquid carrier.

Examples of component (b) (i.e. the at least one other biologically active agent) are: insecticides such as abamectin, acephate, acetamiprid, acetoprole, amidoflumet (S-1955), avermectin, azadirachtin, azinphos-methyl, bifenthrin, bifenazate, bistrifluron, buprofezin, carbofuran, cartap, chlorfenapyr, chlorfluazuron, chlorpyrifos, chlorpyrifos-methyl, chromafenozide, clothianidin, cyflumetofen, cyfluthrin, beta-cyfluthrin, cyhalothrin, gamma-cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, monocrotophos, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, protrifenbute, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tolfenpyrad, tralomethrin, triazamate, trichlorfon and triflumuron; fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflufenamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, etridiazole, famoxadone, fenamidone, fenarimol, fenbuconazole, fencaramid, fenfuram, fenhexamid, fenoxanil, fenpiclonil, fenpropidin, fenpropimorph, fentin acetate, fentin hydroxide, ferbam, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazol, guazatine, imazalil, imibenconazole, iminoctadine, ipconazole, iprobenfos, iprodione, iprovalicarb, isoconazole, isoprothiolane, kasugamycin, kresoxim-methyl, mancozeb, mandipropamid, maneb, mefenoxam, mepanipyrim, mepronil, metalaxyl, metconazole, methasulfocarb, metiram, metominostrobin/fenominostrobin, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxins, probenazole, prochloraz, procymidone, propamocarb, propamocarb-hydrochloride, propiconazole, propineb, proquinazid, prothioconazole, pyraclostrobin, pyrazophos, pyrifenox, pyrimethanil, pyrifenox, pyrrolnitrin, pyroquilon, quinconazole, quinoxyfen, quintozene, silthiofam, simeconazole, spiroxamine, streptomycin, sulfur, tebuconazole, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimorphamid, tricyclazole, trifloxystrobin, triforine, triticonazole, uniconazole, validamycin, vinclozolin, zineb, ziram, and zoxamide; nematocides such as aldicarb, imicyafos, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria such as *Bacillus thuringiensis* subsp. *aizawai*, *Bacillus thuringiensis* subsp. *kurstaki*, and the encapsulated delta-endotoxins of *Bacillus thuringiensis* (e.g., Cellcap, MPV, MPVII); entomopathogenic fungi such as green muscardine fungus; and entomopathogenic virus including baculovirus, nucleopolyhedrovirus (NPV) such as *Helicoverpa zea* nucleopolyhedrovirus (HzNPV), *Anagrapha falcifera* nucleopolyhedrovirus (AfNPV) and granulosis virus (GV) such as *Cydia pomonella* granulosis virus (CpGV).

General references for these agricultural protectants (i.e. insecticides, nematocides, acaricides and biological agents) include *The Pesticide Manual,* 13th Edition, C. D. S. Tomlin, Ed., British Crop Protection Council, Farnham, Surrey, U. K., 2003 and *The BioPesticide Manual*, 2nd Edition, L. G. Copping, Ed., British Crop Protection Council, Farnham, Surrey, U. K. 2001.

Of note is a composition of the present invention wherein component (b) (i.e. the at least one biologically active agent) comprises a biologically active agent selected from the group consisting of abamectin, acephate, acetamiprid, acetoprole, aldicarb, amidoflumet, amitraz, avermectin, azadirachtin, azinphos-methyl, bifenthrin, bifenazate, bistrifluron, buprofezin, carbofuran, cartap, chinomethionat, chlorfenapyr, chlorfluazuron, chlorpyrifos, chlorpyrifos-methyl, chlorobenzilate, chromafenozide, clothianidin, cyflumetofen, cyfluthrin, beta-cyfluthrin, cyhalothrin, gamma-cyhalothrin, lambda-cyhalothrin, cyhexatin, cypermethrin, cyromazine, deltamethrin, diafenthiuron, diazinon, dicofol, dieldrin, dienochlor, diflubenzuron, dimefluthrin, dimethoate, dinotefuran, diofenolan, emamectin, endosulfan, esfenvalerate, ethiprole, etoxazole, fenamiphos, fenazaquin, fenbutatin oxide, fenothiocarb, fenoxycarb, fenpropathrin, fenpyroximate, fenvalerate, fipronil, flonicamid, flucythrinate, tau-fluvalinate, flufenerim, flufenoxuron, fonophos, halofenozide, hexaflumuron, hexythiazox, hydramethylnon, imicyafos, imidacloprid, indoxacarb, isofenphos, lufenuron, malathion, metaflumizone, metaldehyde, methamidophos, methidathion, methomyl, methoprene, methoxychlor, methoxyfenozide, metofluthrin, monocrotophos, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spiridiclofen, spiromesifen, spirotetramat, sulprofos, tebufenozide, tebufenpyrad, teflubenzuron, tefluthrin, terbufos, tetrachlorvinphos, thiacloprid, thiamethoxam, thiodicarb, thiosultap-sodium, tolfenpyrad, tralomethrin, triazamate, trichlorfon, triflumuron, *Bacillus thuringiensis* subsp. *aizawai*, *Bacillus thuringiensis* subsp. *kurstaki*, nucleopolyhedrovirus, an encapsulated delta-endotoxin of *Bacillus thuringiensis*, baculovirus, entomopathogenic bacteria, entomopathogenic virus and entomopathogenic fungi.

Of further note is a composition of the present invention wherein component (b) (i.e. the at least one other biologically active agent) comprises a biologically active agent selected from the group consisting of abamectin, acetamiprid, amitraz, avermectin, azadirachtin, bifenthrin, buprofezin, cartap, chlorfenapyr, chlorpyrifos, clothianidin, cyfluthrin, beta-cyfluthrin, cyhalothrin, lambda-cyhalothrin, cypermethrin, cyromazine, deltamethrin, dieldrin, dinotefuran, diofenolan, emamectin, endosulfan, esfenvalerate, ethiprole, fenothiocarb, fenoxycarb, fenvalerate, fipronil, flonicamid, flufenoxuron, hexaflumuron, hydramethylnon, imidacloprid, indoxacarb, lufenuron, metaflumizone, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spiridiclofen, spiromesifen, tebufenozide, thiacloprid, thiamethoxam, thiodicarb, thiosultap-sodium, tralomethrin, triazamate, triflumuron, *Bacillus thuringiensis* subsp. *aizawai*, *Bacillus thuringiensis* subsp. *kurstaki*, nucleopolyhedrovirus, and an encapsulated delta-endotoxins of *Bacillus thuringiensis*.

Of particular note in the present invention are arthropodicidal suspension concentrate compositions wherein the at least one other biologically active agent is an insecticide or an acaricide including sodium channel modulators such as bifenthrin, cypermethrin, cyhalothrin, lambda-cyhalothrin, cyfluthrin, beta-cyfluthrin, deltamethrin, dimefluthrin, esfenvalerate, fenvalerate, indoxacarb, metofluthrin, profluthrin, pyrethrin and tralomethrin; cholinesterase inhibitors such as chlorpyrifos, methomyl, oxamyl, thiodicarb and triazamate; neonicotinoids such as acetamiprid, clothianidin, dinotefuran, imidacloprid, nitenpyram, nithiazine, thiacloprid and thiamethoxam; insecticidal macrocyclic lactones such as spinetoram, spinosad, abamectin, avermectin and emamectin; GABA (γ-aminobutyric acid)-regulated chloride channel blockers such as endosulfan, ethiprole and fipronil; chitin synthesis inhibitors such as buprofezin, cyromazine, flufenoxuron, hexaflumuron, lufenuron, novaluron, noviflumuron and triflumuron; juvenile hormone mimics such as diofenolan, fenoxycarb, methoprene and pyriproxyfen; octopamine receptor ligands such as amitraz; ecdysone agonists such as azadirachtin, methoxyfenozide and tebufenozide; ryanodine receptor ligands such as ryanodine; nereistoxin analogs such as cartap; mitochondrial electron transport inhibitors such as chlorfenapyr, hydramethylnon and pyridaben; lipid biosynthesis inhibitors such as spirodiclofen and spiromesifen; cyclodiene insecticides such as dieldrin; cyflumetofen; fenothiocarb; flonicamid; metaflumizone; pyrafluprole; pyridalyl; pyriprole; pymetrozine; spirotetramat; and thiosultap-sodium. One embodiment of component (b) (i.e. the at least one other biologically active agent) for mixing with component (a) (i.e. the at least one carboxamide arthropodicide) in the compositions of this invention include nucleopolyhedrovirus such as HzNPV and AfNPV; *Bacillus thuringiensis* and encapsulated delta-endotoxins of *Bacillus thuringiensis* such as Cellcap, MPV and MPVII; as well as naturally occurring and genetically modified viral insecticides including members of the family Baculoviridae as well as entomophagous fungi.

Of note are compositions of the invention wherein the weight ratio of component (b) (i.e. the at least one other biologically active agent) to component (a) (i.e. the at least one carboxamide arthropodicide) ranges from about 1:100 to about 100:1.

The component (c) (i.e. the at least one water-immiscible liquid carrier) in the composition of the present invention provides a liquid fluid medium in which the at least one carboxamide arthropodicide and other solids that may be present are dispersed. Of note is a composition of the present invention comprising component (c) (i.e. the at least one water-immiscible liquid carrier) in an amount typically from about 30 to about 95% by weight, more typically from about 30 to about 80% by weight, even more typically from about 40 to about 70% by weight, and most typically from about 50 to about 60% by weight based on the total weight of the composition.

The term "water-immiscible liquid carrier" as used herein refers to a chemical compound that is liquid at 20° C. and is soluble in water to an extent less than about 2% by weight at 20° C. Of note are compositions of the present invention wherein the at least one liquid carrier is soluble in water to an extent of less than about 0.1%, or less than about 0.01%, or less than about 0.001% by weight at 20° C. Low solubility of liquid compounds in water is a result of low molecular polarity. As the low molecular polarity of the water-immiscible liquid carrier is closer than the high polarity of water to the polarity of carboxamide arthropodicides, carboxamide arthropodicides generally are more soluble in water-immiscible liquid carriers than in water, in which they have little solubility. Nevertheless the amount of component (a) (i.e. the at least one carboxamide arthropodicide) relative to the amount of component (c) (i.e. the at least one water-immiscible liquid carrier) can result in most of the carboxamide arthropodicide being present as solid particles instead of dissolved in the present compositions. In one embodiment of the present compositions component (c) comprises at least one water-immiscible liquid carrier having a viscosity below 50 cP at 20° C. which can facilitate pourability of the composition, and in another embodiment of the present compositions wherein component (c) comprises at least one water-immiscible liquid carrier having a flash point above 65° C. and/or low toxicity (both properties having potential safety benefits).

For certain embodiments of the compositions of the present invention, the at least one water-immiscible liquid carrier can be selected from a fatty acid ester of a $C_1$-$C_4$ alkanol, a vegetable oil and a mineral oil. Not only do these particular water-immiscible liquid carriers have low polarity and work well in the present compositions, but they are relatively nontoxic and are readily available from commercial sources at moderate cost.

Mineral oils, also known as liquid petrolatum, liquid paraffin, paraffin oil and paraffinic oil, comprise a mixture of long-chain, liquid hydrocarbons obtained from petroleum. Mineral oils can be obtained commercially from many sources, either as a straight mineral oil or blended with emulsifiers, for example, Isopar® H (Deutsche Exxon Chemicals) or Suremix® (DuPont, USA).

Vegetable oils are oils obtained from plants. Vegetable oils are typically obtained by pressing or solvent extracting seeds (e.g., sunflower, rapeseed, soybean, corn (maize), linseed (flax)) or fruits (e.g., olive). Examples of vegetable oils that are commercially available at moderate cost are sunflower oil, rapeseed oil, canola oil, soybean oil and corn oil. Vegetable oil mostly comprises fatty acid glycerides, i.e. glycerol esters of fatty acids.

Fatty acid esters of $C_1$-$C_4$ alkanols (i.e. fatty acids esterified with $C_1$-$C_4$ alkanols instead of glycerol) have lower viscosities than vegetable oils and can be particularly useful as the at least one water-immiscible liquid carrier for the present compositions.

The fatty acid portions of the fatty acid esters consist of a carboxylate moiety bound to a hydrocarbon chain, which can be unbranched or branched, but are typically unbranched in natural sources. The hydrocarbon chain can be saturated or unsaturated; typically the hydrocarbon chain is saturated (i.e. alkyl) or contains 1 or 2 carbon-carbon double bonds (i.e. alkenyl). Fatty acid esters formed from fatty acids containing either an odd number of carbon atoms (i.e. even number of carbon atoms in the hydrocarbon chain) or an even number of carbon atoms (i.e. odd number of carbon atoms in the hydrocarbon chain) are useful in the compositions of the present invention. Although esters of lower fatty acids (e.g., containing as few as 4 carbon atoms) can be included in the present compositions, they are preferably mixing with esters of higher fatty acids to decrease the overall polarity, water solubility and volatility. Esters of fatty acids having at least 10 carbon atoms are useful as the water-immiscible liquid carrier for compositions of the present invention for their favorable physical properties. As fatty acids obtained from natural sources typically contain an even number of carbon atoms ranging from 10 to 22 carbon atoms, alkanol esters of these fatty acids are of note for reasons of commercial availability and cost. The $C_{10}$-$C_{22}$ fatty acid esters with an even number of carbon atoms are, for example, erucic acid, lauric acid, palmitic acid, stearic acid, oleic acid, linoleic acid and linolenic acid. Of note are compositions of the present invention wherein component (c) comprises esters of fatty acids containing 12 to 20 carbon atoms. Of further note are compositions of the present invention wherein component (c) comprises esters of fatty acids containing 16 to 18 carbon atoms.

The $C_1$-$C_4$ alkanol-derived portions of the fatty acid esters can be unbranched (i.e. straight-chain) or branched, but are typically unbranched. For reasons including favorable physical properties, commercial availability and cost, of note are the fatty acid esters which are fatty acids esterified with $C_1$-$C_2$ alkanols and of further note is $C_1$ alkanol (i.e. methanol). The fatty acid alkanol esters in a composition of the present invention can also be derived from a mixture of alcohols (e.g., methanol and ethanol).

Fatty acid compositions obtained from natural sources (e.g., seed oils) typically consist of fatty acids having a range of chain lengths and different degrees of unsaturation. Fatty acid ester compositions derived from such fatty acid mixtures can be useful in the compositions of the present invention without need to first separate the fatty acid esters. Suitable fatty acid ester compositions obtained from plants include seed and fruit oils of sunflower, rapeseed, olive, corn, soybean, cotton and linseed. Of note is a composition of the invention wherein component (c) (i.e. the at least one water-immiscible liquid carrier) comprises fatty acid methyl esters derived from seed oils of sunflower, soybean, cotton or linseed. Of particular note is a composition of the invention wherein wherein component (c) comprises fatty acid methyl esters derived from soybean oil (also known as methylated soybean oil or methyl soyate).

Fatty acid esters of alkanols and methods for their preparation are well known in the art. For example, "biodiesel" typically comprises fatty acid esters of ethanol or more commonly methanol. Two principal routes used to prepare fatty acid alkanol esters are transesterification starting with another fatty acid ester (often a naturally occurring ester with glycerol) and direct esterification starting with the fatty acid. A variety of methods are known for these routes. For example, direct esterification can be accomplished by contacting a fatty acid with an alkanol in the presence of a strong acid catalyst such as sulfuric acid. Transesterification can be accomplished by contacting a starting fatty acid ester with the alcohol in the presence of a strong acid catalyst such as sulfuric acid but more commonly a strong base such as sodium hydroxide.

Alkylated seed oils are the transesterification products of seed oils with an alkanol. For example methylated soybean oil, also known as methyl soyate, comprises methyl esters produced by the transesterification of soybean oil with methanol. Methyl soyate thus comprises methyl esters of fatty acids in the approximate molar ratio that the fatty acids occur esterified with glycerol in soybean seed oil. Alkylated seed oils such as methyl soyate can be distilled to modify the proportion of methyl fatty acid esters.

Alkoxylated fatty acid esters, including alkoxylated fatty acid glycerides (also known as alkoxylated triglycerides), are often regarded as "semi-natural" surfactants, as they are made from alkoxylation (ethoxylation or propoxylation) of fatty acid esters of natural origin such as vegetable oil (or seed oil). Common alkoxylated fatty acid esters of vegetable oils include ethoxylated fatty acid esters containing 10 to 60 ethylene oxide-derived units. Fatty acid esters (e.g., triglyceride oils) can be ethoxylated in a process typically involving heating with a catalytic amount of an alkali metal hydroxide or alkoxide, optionally a catalytic amount of an alcohol (e.g., glycerol), and an amount of ethylene oxide depending upon the extent of ethoxylation desired. These conditions apparently ethoxylate alcohol moieties with ethylene oxide to form ethoxylated species (typically comprising multiple ethylene oxide-derived units in a chain), which condense at the terminal end of the ethylene oxide-derived chain with carboxylic moieties to form ester linkages (e.g., through base-catalyzed transesterification), thereby liberating further alcohol moieties, which are then hydroxylated and condensed with carboxylic moieties to form esters. Ethoxylation continues until the quantity of ethylene oxide added is consumed. Under these conditions, hydroxyl groups on alkyl or alkenyl chains of carboxylic acid (e.g., ricinoleic acid in castor oil) may also be hydroxylated. Ethoxylated fatty acid esters and procedures for their preparation are described in U.S. Pat. No. 4,536,324. Fatty acid esters can be propoxylated by substituting propylene oxide for all or part of the ethylene oxide in alkoxylation procedures. For compositions of the present invention, POE 25 castor oil, POE 30 soybean oil and POE 30 rapeseed oil are particularly useful as component (c). The alkoxylated fatty acid esters typically are considered as non-ionic surfactants, but can also be used as water-immiscible liquid carrier having self-emulsifying ability.

Generally, in order for component (c) to form as finely dispersed droplets upon dilution with water, one or more emulsifiers (i.e. a type of surfactant) are needed in the compositions of this invention. However, in certain compositions of the invention, component (c) (i.e. the at least one water-immiscible liquid carrier) has self-emulsifying capability; for example, when component (c) comprises ethoxylated fatty acid esters such as ethoxylated soybean oil (POE 20-30), component (d) (i.e. the at least one emulsifier) can be omitted from the present compositions. Of note are compositions of the present invention wherein component (c) comprises self-emulsifying liquid carriers such as ethoxylated fatty acid esters, then the amount of component (d) (i.e. the at least one emulsifier) can be 0% of the composition by weight.

Surfactants (also known as "surface-active agents") generally modify, and most often reduce, the surface tension of a liquid. Depending on the nature of the hydrophilic and lipophilic groups in a surfactant molecule, surfactants can be useful as wetting agents, dispersing agents (i.e. dispersants), emulsifiers or anti-foaming agents (i.e. defoamers). Surfactants are described as anionic, non-ionic or cationic surfactants based on the chemical nature of their hydrophilic groups. Typical surfactants are described in *McCutcheon's 2005, Volume 1: Emulsifiers and Detergents Annual*, MC Publ. Co., Glen Rock, N.J., as well as Sisely and Wood, *Encyclopedia of Surface Active Agents*, Chemical Publ. Co., Inc., New York, 1964.

An anionic surfactant is a surface-active molecule in which the hydrophilic group connected to the lipophilic portion of the molecule forms a negative ion (i.e. anion) when placed in aqueous solution. Carboxylate, sulfate, sulfonate and phosphate are the hydrophilic groups commonly found in anionic surfactants. Examples of anionic surfactants include sodium alkylnaphthalene sulfonates, naphthalenesulfonate formaldehyde condensates, alkylbenzenesulfonates, lignin sulfonates, alkyl sulfates, alkyl ether sulfates, dialkyl sulfosuccinates, N,N-dialkyltaurates, polycarboxylates, phosphate esters, ethoxylated tristyrylphenol phosphate salts and alkali salts of fatty acids.

A non-ionic surfactant is a surface-active molecule that does not contain ionizable polar end groups but does contain hydrophilic and lipophilic portions. Examples of non-ionic surfactants include ethoxylated alcohols, ethoxylated alkylphenols, ethoxylated sorbitol esters, ethoxylated fatty acid esters, polyoxyethylene/polyoxypropylene block copolymers, glycerol esters, and alkylpolyglycosides where the number of glucose units, referred to as degree of polymerization (D.P.), can range from 1 to 3 and the alkyl units can range from $C_6$ to $C_{14}$ (see *Pure and Applied Chemistry* 72, 1255-1264). As is well known in the art, in these surfactants "ethoxylated" refers to the presence of chains comprising one or more oxyethylene units ($-OCH_2CH_2-$) formed by reaction of ethylene oxide with hydroxyl groups on the sorbitan, sorbitol or fatty acid components, respectively. In ethoxylated sorbitan esters and ethoxylated sorbitol esters, the hydroxyl groups present after ethoxylation are esterified. If more than one oxyethylene unit is generally present on each surfactant molecule, "polyoxyethylene" can be included in the surfactant name, or alternatively a POE (polyoxyethylene) number can be included in the name to indicate the average number of oxyethylene units per molecule.

A cationic surfactant is a surface-active molecule in which the hydrophilic group connected to the lipophilic portion of the molecule forms a positive ion (i.e. cation) when placed in aqueous solution. Examples of cationic surfactants include quaternary ammonium salts such as ethoxylated fatty amines, benzylalkylammonium salts, pyridinium salts and quaternary imidazolium compounds.

The ability of surfactants to reduce surface tension depends upon the molecular structure of the surfactant. In particular, the balance of lipophilic to hydrophilic groups influences whether the surfactant is soluble in water and whether water-immiscible liquid droplets can be stabilized (e.g., emulsified) in water. The HLB number of a surfactant indicates the polarity of the molecules in an arbitrary range of 1-40, with the most commonly used surfactants having a value between 1 to 20. The number increases with increasing hydrophilicity. Surfactants with HLB numbers between 0 and 7 are considered lipophilic, surfactants with HLB numbers between 12 and 20 are considered hydrophilic, and surfactants with HLB numbers between 7 and 12 are considered intermediate.

Examples of hydrophilic surfactants include sodium, calcium and isopropylamine salts of branched or linear alkylbenzenesulfonates. Non-ionic surfactants such as ethoxylated castor oil, ethoxylated sorbitan oleates, ethoxylated alkyl phenols and ethoxylated fatty acids can be in the intermediate HLB range, depending upon chain length and degree of ethoxylation. Triesters of oleic acid and sorbitan (i.e. sorbitan trioleate) and triesters of stearic acid and sorbitan (i.e. sorbitan tristearate) are examples of lipophilic surfactants. Lists of surfactants and their respective HLB numbers have been published widely, for example in A. W. Adamson, *Physical Chemistry of Surfaces*, John Wiley and Sons, 1982.

Surfactants that are useful as emulsifiers typically reside at the oil-water interface with their lipophilic portion immersed in the water-immiscible liquid droplets and their hydrophilic portion penetrating the surrounding aqueous phase, thereby causing reduction of surface tension. Emulsifiers can prevent the coalescence of water-immiscible liquid droplets in water and thus help maintain stable dispersions of water-immiscible liquid droplets in aqueous phase, which are known as emulsions. Thus in the context of the present composition, the emulsifiers facilitate the formation of dispersions of droplets comprising component (c) (i.e. the at least one water-immiscible liquid carrier)(e.g., the hydrophobic oil), component (a) (i.e. the at least one carboxamide arthropodicide), and other components including optionally component (b) (i.e. the at least one other biologically active agent) when the suspension concentrate composition is diluted with water, for example, forming a spray mixture before a spray application.

In one embodiment of the compositions of the present invention, component (d) (i.e. the at least one emulsifier) is selected from an anionic surfactant and a non-ionic surfactant.

For reasons including favorable physical properties, commercial availability and cost, of note are anionic surfactants selected from linear (unbranched) alkylbenzenesulfonates and branched alkylbenzenesulfonates. Of particular note are anionic surfactants, which are linear alkylbenzenesulfonates. Of further note are compositions of the present invention wherein component (d) comprises at least one anionic surfactant in the class of dodecylbenzenesulfonates, for example, calcium dodecylbenzenesulfonate (e.g, Rhodacal® 70/B (Rhodia) or Phenylsulfonat® CA100 (Clariant)) or isopropylammonium dodecylbenzenesulfonate (e.g., Atlox® 3300B (Croda)).

For reasons including favorable physical properties, commercial availability and cost, of note are non-ionic surfactants selected from ethoxylated sorbitan esters, ethoxylated sorbitol esters, ethoxylated fatty acid esters (also known as ethoxylated triglycerides), and mixtures thereof. Ethoxylated sorbitan esters of note are ethoxylated sorbitan oleate (i.e. monooleate, trioleate), ethoxylated sorbitan laurate (i.e. trilaurate), each having 10-30 oxyethylene units (i.e. POE 10 to POE 30). Ethoxylated sorbitol esters of note are ethoxylated sorbitol oleate (i.e. hexaoleate), ethoxylated sorbitol laurate (i.e. hexalaurate). Ethoxylated fatty acid esters of note are ethoxylated seed oils such as ethoxylated soybean oil, ethoxylated castor oil and ethoxylated rapeseed oil, each having 10-30 oxyethylene units (i.e. POE 10 to POE 30). Of note are compositions of the present invention wherein component (d) (i.e. the at least one emulsifier) comprises at least one non-ionic surfactant selected from ethoxylated sorbitan esters (e.g., POE 20 sorbitan trioleate, POE 20 sorbitan monooleate), ethoxylated sorbitol esters (e.g., POE 40 sorbitol hexaoleate), and ethoxylated seed oils (e.g., POE 30 soybean oil, POE 25 castor oil, POE 30 rapeseed oil). Examples of suitable non-ionic surfactants include Emsorb 6900 (Cognis), Tween® 80 (Croda), Cirresol® G-1086 (Croda), Agnique SBO-30 (Cognis) and Trylox 5904 (Cognis).

Mixtures of emulsifier compounds are one embodiment of component (d) of the present composition and can be used to facilitate adjusting overall HLB to provide optimal performance. While the relative amounts of component (d) need to be adjusted to achieve best results for a particular combination of component (c) (i.e. the at least one water-immiscible liquid carrier), active ingredients (i.e. component (a) and optionally component (b)) and other components, optimal results for compositions of the present invention comprising a water-immiscible liquid carrier selected from a vegetable oil, a mineral oil, an ethoxylated seed oil and an alkylated seed oil are typically achieved with an emulsifier mixture having HLB numbers in the range from about 8 to about 15, and more particularly in the range from about 8 to about 12. The HLB number of an emulsifier mixture is calculated as the sum of the products of the mass fraction of each emulsifier component multiplied by its respective HLB number. For example, a 6:4 mixture of a POE 30 castor oil (HLB 11.8) with an ethoxylated sorbitol hexaoleate (HLB 10.5) would have a HLB number of 11.3. Adding a sorbitan monolaurate (HLB 8.6) to a level of 30% and reducing the ethoxylated sorbitol hexaoleate to 20%, with the remainder being the POE 30 castor oil (i.e. 50%), would reduce the HLB number of the emulsifier mixture to 10.6.

The composition of the present invention generally comprises component (d) (i.e. the at least one emulsifier) in an amount typically from 0 to about 50% by weight, more typically from about 2 to about 50% by weight, even more typically from about 10 to about 40% by weight, and most typically from about 20 to about 30% by weight based on the total weight of the composition. The composition of the present invention can comprise a mixture of an anionic surfactant and an non-ionic surfactant as the at least one emulsifier wherein the weight ratio of the anionic surfactant to the non-ionic surfactant ranges from about 2:1 to about 1:10, or from about 2:1 to about 1:5. In one embodiment of the present invention the weight ratio of the at least one emulsifier to the at least one liquid carrier ranges from about 1:1 to about 1:20.

Thickeners are organic or inorganic liquid or solid additives that increase the viscosity of suspension concentrate compositions. Greater viscosity is desirable for slowing sedimentation of suspended solid particles and for reducing phase separation during storage. Phase separation usually eventually occurs in unstructured organic dispersions and suspension concentrates. Significant phase separation of a suspension concentrate composition can be perceived as a sign of poor quality. Suspension concentrate compositions having less than 5 percent phase separation are particularly desirable, but suspension concentrate compositions having up to about 20 percent phase separation can be acceptable. Thickeners are typically added to a suspension concentrate composition at low concentrations to allow the composition formulation to accommodate other ingredients. An extensive list of thickeners and their applications can be found in *McCutcheon's 2005, Volume 2: Functional Materials* published by MC Publishing Company.

Thickeners comprising silica have been found to work well in combination with the other components in the compositions of the present invention. Without being bound by any particular theory, the silica is believed to increase viscosity through formation of a loose network structure comprising dispersed silica particles, which are held together by hydrogen bonding and long-range electrostatic forces. Silica compositions are commercially manufactured by precipitation, spray drying or high temperature flame hydrolysis (fumed silica). Free silanol (Si—OH) groups on the surface makes silica generally hydrophilic unless the silanol groups are capped with hydrophobic groups such as through contact with chlorotrimethylsilane and 1,1,1,3,3,3-hexamethyldisilazane. Although such hydrophobic surface-treated silica can be used in the present compositions, they are expensive and a greater amount is needed.

Particularly useful as a silica thickener in the compositions of the present invention is fumed silica such as Aerosil® 200 (Degussa AG) or Cab-O-Sil M5 (Cabot Corp.). Not only is the fumed silica hydrophilic, but it is also comprised of submicron particle aggregates with a surface area in excess of 100 $m^2/g$. Such small silica particles with large surface areas promote the development of structure, thus increasing viscosity. Coarser precipitated or spray dried silica can also be used for thickening the present compositions; however, better results can be achieved if the size of the silica particles is reduced through milling or other means to provide comparable surface areas. Of note for increasing the viscosity of the present compositions, particularly those compositions comprising a vegetable oil, a mineral oil or an alkylated seed oil, are silica thickeners where the surface area of the silica is at least 20 $m^2/g$.

Another advantage of hydrophilic fumed silica is that it has a slightly acidic pH, for example pH 4-6 for Aerosil® 200, which helps prevent chemical degradation of base-sensitive compounds such as the at least one carboxamide anthranilamide of Formula 1, an N-oxide or a salt thereof. Some precipitated silica and surface treated silica have pH values ranging from around neutral to even alkaline (i.e. pH greater than 7). Therefore hydrophilic fumed silica is of note for the silica thickener in the composition of the present invention. Of particular note is the composition of this invention wherein component (e) (i.e. the silica thickener) comprises fumed silica such as Aerosil® 200 in an amount typically from about 0.01 to about 5% by weight, and more typically from about 0.5 to about 5% by weight based on the total weight of the composition.

To obtain adequate viscosity of the present compositions, a silica thickener alone is generally not sufficient in the relatively small amounts that can be accommodated in a formulation. However, this problem is now discovered to be solved by including in the present composition about 0.1 to about 10% by weight of component (f) (i.e. the at least one protic solvent) selected from water, a $C_1$-$C_{12}$ alkanol and a $C_2$-$C_3$ glycol, which function cooperatively with the silica thickener and potentiate its performance to provide sufficient viscosity. Without being bound by any particular theory, one possibility for the benefits provided by this coupling is that the at least one protic solvent in contact with the silica thickener extends the range of interaction forces between silica particles of the silica thickener and thus increases the viscosity of the arthropodicidal suspension concentrate composition. $C_1$-$C_{12}$ alkanols include straight and branched chain alkanols containing 1 to 12 carbon atoms. Of note is that compositions of the present invention wherein component (f) comprises a $C_1$-$C_4$ alkanol. $C_2$-$C_3$ glycols include ethylene glycol and propylene glycol. In one embodiment component (f) comprises a protic solvent select from water, methanol, ethanol and ethylene glycol. For reasons of cost and environmental safety, of note is an arthropodicidal suspension concentrate composition wherein the at least one protic solvent is water. The composition of the present invention generally comprises at least one protic solvent in an amount from about 0.1 to about 10% or from about 0.5 to about 5% by weight based on the total weight of the composition. When the at least one protic solvent is water, it needs not be added to the composition of the invention as a separate ingredient provided that other ingredients in the composition contain a sufficient amount of water.

Including component (f) (i.e. the at least one protic solvent) in the present composition also surprisingly solves another problem. In the absence of component (f), the arthropodicidal suspension concentrate composition can form a stiff gel after exposure to elevated temperature. By "elevated temperature" is meant a temperature higher than 45° C. Such gels can be difficult to reliquify, and they can increase the residue remaining in a container after the composition is poured out of the container. Including component (f) in the present composition can reduce, and in some instances, even eliminate the formation of a gel. Furthermore even when a gel does form in the presence of component (f), the gel is generally weak, e.g. easily breakable and reliquifies upon mild shaking of the container, thus minimizing residue remaining in the container after pouring out the composition. Such weak gels also have an advantage of helping prevent settling and phase separation. Without being bound by any particular theory, one possibility for the formation of a weak gel is if a gel results from the interaction between component (a) (i.e. the at least one carboxamide arthropodicide) and component (c) (i.e. the at least one water-immiscible liquid carrier), component (f) such as water, may surround the carboxamide arthropodicide and effectively render it more polar, and therefore less lipophilic and less attractive to the lipophilic water-immiscible liquid carrier.

Although inclusion of component (f) can reduce gelling and potentiate the effect of the silica thickener to provide adequate viscosity, component (f) in combination with component (e) (i.e. the silica thickener) can also potentiate degradation of sensitive carboxamide arthropodicides even when the silica thickener comprises mildly acidic fumed silica. However, this problem is now discovered to be solved by including component (g) (i.e. the at least one water-soluble carboxylic acid) in an amount ranging from about 0.001 to about 5% by weight based on the total weight of the composition. Furthermore component (g) can also help thicken the formulation. Water-soluble carboxylic acids refer to organic compounds comprising at least one carboxylic acid group and which are soluble in water at 20° C. to an extent of at least about 0.1% by weight. Useful water-soluble carboxylic acid typically contains from 1 to 10 carbon atoms, and can contain heteroatoms, including substituents such as halogen and hydroxy. Hydroxy substituents can also be used to increase the water solubility of the at least one carboxylic acid. Of note in preventing degradation of component (a) (i.e. the at least one carboxamide arthropodicide), a composition of the present invention comprises at least one carboxylic acid where the most acidic carboxylic acid group on the carboxylic acid has a $pK_a$ below about 5 but above about 2. Without being bound by any particular theory, the presence of component (g) is believed to increase the ionic strength of component (f) (i.e. the at least one protic solvent) surrounding the silica particles of the silica thickener and thus facilitates the electrostatic interactions between silica particles, resulting in increased viscosity. As long chain carboxylic acids can potentially interfere sterically with the interaction between silica particles, short-chain carboxylic acids with molecular weights not exceeding 300 g/mol are of note for component (f) in the present composition. Examples of suitable water-soluble carboxylic acids include acetic acid, propionic acid and citric acid. For reasons including low volatility as well as commercial availability and low cost, citric acid is of note as the at least one water-soluble carboxylic acid in the present composition. The composition of the present invention generally comprises component (f) (i.e. at least one water-soluble carboxylic acid) in an amount about 0.001 to about 5%, more typically about 0.01 to about 5%, and most typically about 0.01 to about 2% by weight based on the total weight of the composition.

Other formulation ingredients can be used in the present invention such as rheology modifiers, wetting agents, dyes, deformers and the like. These ingredients are known to one skilled in the art and can be found described, for example, in *McCutcheon's* 2005, *Volume 2: Functional Materials* published by MC Publishing Company.

Methods for making suspensions and dispersions of particles are well known and include ball-milling, bead-milling, sand-milling, colloid milling and air-milling combined with high-speed blending, and such methods can be useful in the preparation of the arthropodicial suspension concentrate compositions of the present invention. The desired method for applying the diluted compositions of the present invention, such as spraying, atomizing, dispersing or pouring, will depend on the desired objectives and the given circumstances, and can be readily determined by one skilled in the art.

Although the arthropodicidal suspension concentrate composition of the present invention can be applied directly to an arthropod pest or its environment, the arthropodicidal suspension concentrate composition is ordinarily first diluted with water to form a diluted composition, and then the arthropod pest or its environment is contacted with an effective amount of the diluted composition to control the arthropod pest. Upon mixing with water, the present arthropodicidal suspension concentrate composition forms an emulsion of droplets of component (c) (i.e. the at least one water-immiscible liquid carrier) comprising suspended solid particles of component (a) (i.e. the at least one carboxamide arthropodicide) and other components including optionally component (b). This diluted composition can be applied to an arthropod pest or its environment by a variety of means including spraying. The present arthropodicidal suspension concentrate compositions after dilution with water, spraying and then drying have been discovered to provide remarkably effective control of arthropod pests (e.g., killing the pests, interfering with their growth development or reproduction, and/or inhibiting their feeding) that is resistant to subsequent wash-off (e.g., on exposure to rain).

To supplement the adjuvants contained in pesticide formulations, separately formulated adjuvant products can be added to spray tank mixtures. These additional adjuvants are commonly known as "spray adjuvants" or "tank-mix adjuvants", and include any substance mixed in a spray tank to improve the performance of a pesticide treatment, such as by enhancing efficacy (e.g., biological availability, adhesion, penetration, uniformity of coverage and durability of protection), or minimizing or eliminating spray application problems associated with incompatibility, foaming, drift, evaporation, volatilization and degradation. As no single adjuvant generally can provide all these benefits, compatible adjuvants are often combined to perform multiple functions. To obtain optimal performance, adjuvants are selected with regard to the properties of the active ingredient, formulation and target (e.g., crops, arthropods).

Among the spray adjuvants, oils including crop oils, crop oil concentrates, vegetable oil concentrates and methylated seed oil concentrates are used to improve the efficacy of pesticides, possibly by means of promoting more even and uniform spray deposits. Products identified as "crop oil" typically contain 95 to 98% paraffin or naphtha-based petroleum oil and 1 to 2% of one or more surfactants functioning as emulsifiers. Products identified as "crop oil concentrates" typically consist of 80 to 85% of emulsifiable petroleum-based oil and 15 to 20% of non-ionic surfactants. Products correctly identified as "vegetable oil concentrates" typically consist of 80 to 85% of vegetable oil (i.e. seed or fruit oil, most commonly from cotton, linseed, soybean or sunflower) and 15 to 20% of non-ionic surfactants. Adjuvant performance can be improved by replacing the vegetable oil with methyl esters of fatty acids that are typically derived from vegetable oils. Examples of methylated seed oil concentrates include MSO® Concentrate from UAP-Loveland Products, Inc. and Premium MSO Methylated Spray Oil from Helena Chemical Company. The amount of oil-based adjuvants added to spray mixtures generally does not exceed about 2.5% by volume, and more typically the amount is from about 0.1 to about 1% by volume. The application rates of oil-based adjuvants added to spray mixtures are typically between about 1 to about 5 L per hectare, and methylated seed oil-based adjuvants in particular are typically used at a rate from about 1 to about 2.5 L per hectare.

Spray adjuvants containing mixtures of emulsifiers with oils, particularly methylated seed oils, are found to be compatible in tank mixtures with the present arthropodicidal suspension concentrate compositions. Furthermore, spray mixtures comprising methylated seed oil adjuvants in addition to the present compositions are found to provide remarkably improved control efficacy on certain arthropod pests (such as for protecting plants from such arthropod pests). Therefore one embodiment of the present invention relates to a method for controlling an arthropod pest, comprising diluting an arthropodicidal suspension concentrate composition of the present invention with water, and optionally adding an adjuvant such as a methylated seed oil (in any order of addition or mixing) to form a diluted composition, and contacting the arthropod pest or its environment with an effective amount of said diluted composition.

The ratio of the volume of arthropodicidal suspension concentrate composition to the volume of water used to dilute it is generally in the range from about 1:100 to about 1: 1000, more typically from about 1:200 to about 1:800, and most typically from about 1:300 to about 1:600. The amount of diluted composition needed for effective control of an arthropod pest depends upon a variety of factors including the concentration of the at least one carboxamide arthropodicide in the arthropodicidal suspension concentrate composition, the extent of dilution in water, the susceptibility of the arthropod pest to the at least one carboxamide arthropodicide and environmental conditions as well as the concentration of other adjuvants, but can be easily determined by calculation and simple experimentation by one skilled in the art.

Without further elaboration, it is believed that one skilled in the art using the preceding description can utilize the present invention to its fullest extent. The following Examples are, therefore, to be construed as merely illustrative and not limiting of the disclosure in any way whatsoever.

General Procedure for Preparing a Suspension Concentrate Composition

The following general procedure was used for Examples A-E and Comparative Examples A-E. Table 1 lists chemical identities for the ingredients, and Tables 2A and 2B list amounts used in the compositions of Examples A-E and Comparative Examples A-E. In a 250-mL stainless steel beaker equipped with a overhead stirrer, a liquid carrier, a carboxamide arthropodicide, emulsifiers and other ingredients (as specified for each Example) were mixed with stirring to make 100 g of a mixture. The mixture was homogenized using a rotor stator mixer (Polytron PT 3000, Kinematica AG, Switzerland), and then milled to about 1 micron median particle size using a 50 mL Eiger Motormill (a horizontal bead mill manufactured by Eiger Machinery Inc., Chicago, Ill.) to afford a suspension concentrate.

TABLE 1

Identity of Ingredients used in Examples

| Name | Identity |
|---|---|
| Compound 1 | 3-bromo-1-(3-chloro-2-pyridinyl)-N-[4-cyano-2-methyl-6-[(methylamino)carbonyl]phenyl]-1H-pyrazole-5-carboxamide |
| Compound 2 | 3-bromo-N-[4-chloro-2-methyl-6-[(methylamino)carbonyl]phenyl]-1-(3-chloro-2-pyridinyl)-1H-pyrazole-5-carboxamide, |
| Agnique ® ME 18SDU (Cognis Corp) | Methylated soybean oil |
| Cirrasol ™ G-1086 (Croda) | Polyoxyethylene (40) sorbitol hexaoleate |
| Agnique ® BL2707 (Cognis Corp) | Mixture of Ca dodecylbenzenesulfonate & POE30 ethoxylated castor oil |
| Aerosil ® 200 (Degussa AG) | Fumed silica |
| Cab-O-Sil ® M5 (Cabot Corp.) | Fumed silica |

The sample of Compound 1 used in the present Examples and Comparative Examples was prepared as described in Reference Example 1. The sample of Compound 2 used in the present Examples and Comparative Examples was a blend of products prepared using methods described in PCT Publications WO 03/015519 A1 and WO 2006/062978, and melted in the range between 234 and 236° C.

Reference Example 1

Preparation of 3-bromo-1-(3-chloro-2-pyridinyl)-N-[4-cyano-2-methyl-6-[(methylamino)carbonyl]phenyl]-1H-pyrazole-5-carboxamide To a mixture of 3-bromo-1-(3-chloro-2-pyridinyl)-1H-pyrazole-5-carboxylic acid (20.6 kg) and 2-amino-5-cyano-N,3-dimethylbenzamide (14.1 kg) in acetonitrile (114 kg) was added 3-picoline (22.2 kg). The mixture was cooled to −10 to −14° C., and then methanesulfonyl chloride (10.6 kg) was slowly added so that the temperature did not exceed 5° C. After reaction completion as ascertained by HPLC and NMR analyses, the mixture was worked up by successively adding water (72.6 kg) and concentrated hydrochloric acid (7.94 kg) at such a rate that the temperature did not exceed 5° C. After being maintained at a temperature not exceeding 5° C. for about 30 minutes, the reaction mixture was filtered to collect the solid product, which was successively washed with acetonitrile-water (2:1, 2×12.3 kg) and acetonitrile (2×10.4 kg). The solid was then dried at about 50° C. under reduced pressure and a flow of nitrogen gas to give the title product as a white crystalline solid, which was directly used in the present formulation Examples and Comparative Examples. With a moderate rate of heating (heating to about 150° C. over 5 minutes and then decreasing rate of heating from about 4-5° C./minute to about 3° C./minute to reach 210° C. over about 15 minutes more) to facilitate volatilization of loosely entrained solvents from the solid product, melting occurred in the range between 204 and 210° C.

Evaluation of Chemical, Physical Stability and Pourability of Suspension Concentrates The chemical stability of each example was evaluated by aging samples in heated ovens (i.e. at 54° C. for 2 weeks) and then comparing the content of the carboxamide arthropodicide before and after aging. Carboxamide arthropodicide content was determined by assaying the compositions with high-pressure liquid chromatography (HPLC) using reverse phase columns. The percent relative decomposition was calculated by subtracting the final weight percent of carboxamide arthropodicide from the initial weight percent of carboxamide arthropodicide, then dividing the difference by the initial weight percent of carboxamide arthropodicide, and then multiplying the resulting quotient by 100%.

The physical stability of the suspension concentrate examples was determined by measuring the extent of phase separation of the oven-aged samples. The degree of phase separation was determined by measuring with a ruler the thickness of the layer of water-immiscible carrier devoid of suspended particles and the total height of liquid material in the sample bottle, and then dividing the thickness of separated water-immiscible carrier by the total height of liquid material, and multiplying the quotient by 100%. If the interface between the separated immiscible carrier and the suspension was not even, several measurements were made and the results averaged.

The pourability of the suspension concentrate examples was determined by pouring out the oven-aged sample, and then measuring the weight of residue in the sample container. The percent residue was calculated by dividing the residue weight by the sample weight, and multiplying the quotient by 100%. The pourability of a suspension concentrate desirably results in less than 5% residue, although, less than 10% residue is acceptable.

TABLE 2A

Compositions of Examples of the Present Invention. Amounts are by weight based on total weight of the composition.

| Ingredient (g) | Example A | Example B | Example C | Example D | Example E |
| --- | --- | --- | --- | --- | --- |
| Compound 1 | 10.0 | 10.0 | 20.0 | 10.0 | — |
| Compound 2 | — | — | — | — | 10.0 |
| Agnique ® ME 18SDU | 51.96 | 54.583 | 43.48 | 54.58 | 54.583 |
| Agnique ® BL2707 | 25.0 | 25.0 | 25.0 | 25.0 | 25.0 |
| Cirresol ® G-1086 | 5.0 | 5.0 | 5.0 | 5.0 | 5.0 |
| Aerosil ® 200 | 4.0 | 1.3 | — | 1.3 | 1.3 |
| Cab-O-Sil ® M5 | — | — | 1.5 | — | — |
| Water | 4.0 | 4.1 | 5.0 | 4.1 | 4.1 |
| Citric acid | 0.04 | 0.017 | 0.02 | 0.02 | 0.017 |

TABLE 2B

Compositions of Comparative Examples. Amounts are by weight based on total weight of the composition.

| Ingredient (g) | Comparative Example A | Comparative Example B | Comparative Example C | Comparative Example D | Comparative Example E |
| --- | --- | --- | --- | --- | --- |
| Compound 1 | 10.0 | 20.0 | 20.0 | 20.0 | 20.0 |
| Agnique ® ME 18SDU | 57.475 | 50.0 | 48.5 | 45.0 | 43.5 |
| Agnique ® BL2707 | 25.0 | 25.0 | 25.0 | 25.0 | 25.0 |
| Cirresol ® G-1086 | 5.0 | 5.0 | 5.0 | 5.0 | 5.0 |
| Cab-O-Sil ® M5 | 0.0 | 0.0 | 1.5 | 0.0 | 1.5 |
| Water | 2.5 | 0.0 | 0.0 | 5.0 | 5.0 |
| Citric acid | 0.025 | 0.0 | 0.0 | 0.0 | 0.0 |

Tables 3A and 3B list results from the chemical stability, physical stability and/or pourability tests.

TABLE 3A

Chemical and Physical Stabilities of Compositions Prepared

|  | % Relative Decomposition | % Phase Separation |
|---|---|---|
| Example A | 1.1 | 0.0 |
| Example B | 1.2 | 3.4 |
| Comparative Example A | 0.81 | 53.0 |

The results listed in Table 3A illustrate the importance of the silica thickener for compositions of the present invention. Comparative Example A having 0% silica thickener showed significantly greater phase separation than Examples A and B, which comprised 4% and 1.3% of silica thickener, respectively.

TABLE 3B

Chemical and Physical Stabilities and Pourability of Compositions Prepared

|  | % Relative Decomposition | % Phase Separation | % Residue after pour-out |
|---|---|---|---|
| Example C | 0.67 | 3.9 | 9.6 |
| Comparative Example B | 0.14 | 0.0 | 100.0 |
| Comparative Example C | 0.14 | 0.0 | 100.0 |
| Comparative Example D | 0.77 | 15.4 | 1.8 |
| Comparative Example E | 0.74 | 3.9 | 12.6 |

The results listed in Table 3B illustrate the importance of the silica thickener, the at least one protic solvent and the at least one water-soluble carboxylic acid. Comparative Examples B and C showed no phase separation, but formed a stiff gel, and thus the oven-aged samples could not be poured out. Comparative Example D having no silica thickener and no citric acid showed greater phase separation and greater % decomposition than Example C. Comparative Example E having no citric acid showed greater % decomposition and poorer pourability than Example C.

BIOLOGICAL EXAMPLES OF THE INVENTION

Test A

For evaluating control of the western flower *thrips* (*Frankliniella occidentalis* Pergande) through contact and/or systemic means, each test unit consisted of a bean plant (var. *Soleil*) with at least two true leaves, which was planted in Redi-earth® medium (Scotts Co.). One plant was considered as one replication; four replications were used per treatment.

Technical material (unformulated) was dissolved in acetone and mixed with water containing 500 ppm of a blend of non-ionic surfactant with organosilicone (Kinetic®, Helena Chemical Co.). Formulated materials were diluted with water only. Rates of the test solutions were reported by the amount of active ingredient in ppm. Plants were sprayed using a TeeJet flat fan spray nozzle positioned 7.5 inches (19 cm) above the tallest plant. Spray flow rate was adjusted to 5.5 mL/sec for an equivalent of 500 L/ha. After spraying of the test solutions, the test units were placed in ventilated enclosures for at least one hour to dry. Thirty adult *thrips* were then added to each unit, and then the plants were placed in enclosed cages to prevent insect egress. The test units were held for 7 days in a growth chamber maintained at 25° C., with a light cycle of 16 h with light (as daytime) and 8 hr in dark (as nighttime). Evaluation was made by counting numbers of immature *thrips* in each test unit. Percent control was calculated by dividing the number of immature *thrips* in a test unit by the number of immature *thrips* in the untreated unit, subtracting the quotient from 1, and then multiplying the difference by 100%. Results are listed in Table 4A.

TABLE 4A

% Control of Western Flower Thrips

| Rate (ppm a.i.) | Example D | Technical Compound 1 |
|---|---|---|
| Untreated | | 0 |
| 100 | 74 | 74 |
| 200 | 78 | 72 |

The results indicate that the Example D composition of the present invention showed levels of efficacy similar to unformulated Compound 1 for controlling western flower *thrips*.

Test B

For evaluating control of silverleaf whitefly (*Bemisia argentifolii* Bellows & Perring), the test unit consisted of a 14-21-day-old cotton plant with at least two true leaves, which was planted in Redi-earth® medium (Scotts Co.). The plants were placed in screened cages, where whitefly adults were introduced and allowed to lay eggs for approximately twenty-four hours. Only plants showing egg lay were used for testing. Before spraying the test solutions, the plants were checked again for egg hatch and crawler settlement. One leaf per plant was considered as one replication; four replications were used per treatment.

Test solutions were formulated as described in TEST A. A control solution consisting of 25% acetone in water was also prepared. After spraying, plants were allowed to dry in a ventilated enclosure and held for six days in a growth chamber at 50% relative humidity, 16 h with light (as daytime) at 28° C. and 8 h in dark (as nighttime) at 24° C. After removing all leaves from each test plant, evaluation was made by counting dead and live nymphs present on the underside of the leaves. Results are listed in Table 4B.

TABLE 4B

% Mortality of Silverleaf Whitefly

| Rate (ppm a.i.) | Example D | Technical Compound 1 |
|---|---|---|
| Control | | 13 |
| 22 | 89 | 90 |
| 66 | 98 | 91 |
| 200 | 100 | 100 |
| 600 | 100 | 100 |

The results indicate that the Example D composition of the present invention showed levels of efficacy similar to unformulated Compound 1 for controlling silverleaf whitefly.

Test C

For evaluating control of green peach aphid (*Myzus persicae*) through contact and/or systemic means, the test unit consisted of a 3-week old radish plant pre-infested with 30-40 aphids 24 h prior to treatment with test solutions. One plant was considered as one replication, four replications were used per treatment.

After spraying of the formulated test solutions, each test unit was allowed to dry, and the test units were held for 6 days in a growth chamber maintained at 19-21° C. and 50-70% relative humidity. Dead and live of aphids were counted in each test unit to determine percent mortality. Results are listed in Table 4C.

TABLE 4C

% Mortality of Green Peach Aphid

| Rate (ppm a.i.) | Example D | Technical Compound 1 |
|---|---|---|
| Untreated |  | 2 |
| 50 | 71 | 8 |
| 100 | 69 | 9 |
| 200 | 95 | 19 |
| 400 | 100 | 35 |

The results indicate that the Example D composition of the present invention showed surprisingly enhanced efficacy compared to unformulated Compound 1 for controlling green peach aphid.

Test D

For evaluating rainfastness (resistance to wash-off) for the control of beet armyworm (*Spodoptera exigua*), the test unit consisted of a cotton plant grown in a pot containing Redi-earth® medium. Test solutions were formulated as described in TEST A. When the plants were at the 4-6 true leaf growth stage, the plants were sprayed with the formulated test solution using a belt sprayer with nozzle positioned 19 cm above the plants and providing an application volume of 234 liters/ha. After spraying of the formulated test solutions, each test unit was allowed to dry for 2 h and then exposed to about 95 mm of simulated rain in a greenhouse. Plants were then allowed to dry, and leaves were cut and placed on agar in 16-cell plastic trays. One 3-day-old, laboratory reared beet armyworm larva was placed in each cell, and the cells were covered with a plastic lid. Two 16-cell trays were used per treatment. Trays were held in a growth chamber at 75% relative humidity, 16 h with light (as daytime) and 8 h in dark (as nighttime) at 25° C. Four days after infestation, each test unit was evaluated for larvae mortality, and the mean concentrations killing 50% of the population (mean $LC_{50}$) were calculated and are listed in Table 4D.

TABLE 4D

Mean $LC_{50}$ of Beet Armyworm

| Test | Composition | Rain | Mean LC50 (g a.i./Ha) |
|---|---|---|---|
| 1 | Example D | Yes | 20 |
| 2 | Technical Compound 1 | Yes | Very little activity |
| 3 | Example E | No | 0.7 |
| 4 | Technical Compound 2 | No | 4 |
| 5 | Example E | Yes | 4 |
| 6 | Technical Compound 2 | Yes | Inactive |

Test results in Table 4D demonstrate that even in the absence of simulated rain, the Example E composition of the present invention showed markedly enhanced efficacy compared to unformulated Compound 2 ($LC_{50}$ 0.7 vs. 4) for controlling beet armyworm. The difference was even more dramatic after exposure to simulated rain. Although the efficacy of the Example E composition dropped from an $LC_{50}$ of 0.7 to 4, this is still quite high activity. In contrast, the efficacy of unformulated Compound 2 dropped from an $LC_{50}$ of 4 to no detectable activity. Also after simulated rain, the Example D composition of the present invention still showed an $LC_{50}$ of 20, whereas unformulated Compound 1 showed very little activity. These results indicate that the compositions of the present invention have much better rainfastness and resistance to wash-off compared to the unformulated active arthropodicides. The rainfastness and wash-off resistance of the present compositions makes these compositions particularly useful for controlling arthropod pests in crop fields, orchards and other areas subject to rainfall.

Test E

To evaluate the effect of methylated seed oil as an adjuvant for the present composition for controlling silverleaf whitefly (*Bemisia argentifolii*), the test unit consisted of a 14-21-day-old cotton plant with at least two true leaves, which was planted in Redi-earth® medium (Scotts Co.). The plants were placed in screened cages, where whitefly adults were introduced and allowed to lay eggs for approximately twenty-four hours. Only plants showing egg lay were used for testing. Before spraying the test solutions, the plants were checked again for egg hatch and crawler settlement. One leaf per plant was considered as one replication; four replications were used per treatment.

The Example B composition was diluted with water to provide a spray mixture containing specified concentrations of the active ingredient (Compound 1). Spray mixtures were also prepared to contain not only the diluted Example B composition but also three concentrations (500, 1000 or 3000 ppm) of Premium MSO Methylated Spray Oil adjuvant, a proprietary blend of methylated vegetable oils and non-ionic surfactants marketed by Helena Chemical Company, Collierville, Tenn.

Plants were sprayed using a TeeJet flat fan spray nozzle positioned 7.5 inches above the tallest plant. Spray flow rate was 5.5 mL/sec to deliver an equivalent of 500 L/ha. After spraying, plants were allowed to dry in a ventilated enclosure and then moved to a growth chamber providing 16 h of light (as daytime) at 28° C. and 8 h of darkness (as nighttime) at 24° C. and 50% relative humidity.

Six days after plants were sprayed, evaluations were made by removing all leaves from each test plant, and counting the number of dead and live nymphs present on the underside of the leaves; the data are listed in Table 4E. In addition, the mean concentrations killing 50% of the population (mean $LC_{50}$) were calculated and are also listed in Table 4E.

TABLE 4E

% Mortality of Silverleaf Whitefly

| Concentration of a.i. (ppm) | Concentration of methylated seed oil based adjuvant (ppm) | | | |
|---|---|---|---|---|
| | 0 | 500 | 1000 | 3000 |
| 75 | 15 | 44 | 87 | 100 |
| 150 | 56 | 83 | 88 | 100 |
| 300 | 91 | 99 | 99 | 100 |
| 600 | 100 | 99 | 99 | 100 |

TABLE 4F

Effects of Adjuvant Concentration on Mean $LC_{50}$ of Silverleaf Whitefly

| Concentration of adjuvant (ppm) | Mean $LC_{50}$ (ppm a.i.) | | | |
|---|---|---|---|---|
| | 0 | 500 | 1000 | 3000 |
| | 121 | 64 | 27 | * |

* $LC_{50}$ cannot be calculated as all rates gave 100% mortality.

The data demonstrate that the addition of the adjuvant as a spray tank mixture with the Example B composition greatly enhanced efficacy. As shown in Table 4E, the spray mixture containing 75 ppm of the active ingredient and 3000 ppm of the adjuvant as a tank mix was as effective as the spray mixture containing 600 ppm of active ingredient with no adjuvant, the adjuvant increased potency by at least about 8-fold. The $LC_{50}$ data listed in Table 4F show that 500 ppm of the adjuvant added as a tank mix provided a 2-fold increase in potency of the active ingredient, and 1000 ppm provided a 4.5-fold increase in potency. The magnitude of the efficacy enhancement resulting from addition of the methylated seed oil-based adjuvant is particularly remarkable considering that the Example B composition itself contained 56% methyl soyate as well as emulsifiers.

What is claimed is:

1. An arthropodicidal suspension concentrate composition comprising by weight based on the total weight of the composition:
   (a) about 0.1 to about 40% of at least one carboxamide arthropodicide that is solid at room temperature;
   (b) 0 to about 20% of at least one biologically active agent other than the at least one carboxamide arthropodicide that is solid at room temperature;
   (c) about 30 to about 95% of at least one water-immiscible liquid carrier selected from the group consisting of a methylated seed oil of sunflower, soybean, cotton or linseed;
   (d) about 2 to about 50% of at least one emulsifier comprising a mixture of a dodecylbenzenesulfonate and an ethoxylated sorbitol hexaoleate;
   (e) about 0.01 to about 10% of a silica thickener comprising fumed silica;
   (f) about 0.1 to about 10% of water; and
   (g) about 0.001 to about 5% of citric acid;
wherein component (a) is selected from anthranilamides of Formula 1, N-oxides, and salts thereof <chemical structure of Formula 1> wherein
   X is N, CF, CCl, CBr or Cl;
   $R^1$ is $CH_3$, Cl, Br or F;
   $R^2$ is H, F, Cl, Br or —CN;
   $R^3$ is F, Cl, Br, $C_1$-$C_4$ haloalkyl or $C_1$-$C_4$ haloalkoxy;
   $R^{4a}$ is H, $C_1$-$C_4$ alkyl, cyclopropylmethyl or 1-cyclopropylethyl;
   $R^{4b}$ is H or $CH_3$;
   $R^5$ is H, F, Cl or Br; and
   $R^6$ is H, F, Cl or Br.

2. The composition of claim 1 wherein component (a) is from about 5 to about 25% of the composition by weight; component (b) is from 0 to about 15% of the composition by weight; component (c) is from about 40 to about 70% of the composition by weight; component (d) is from about 10 to about 40% of the composition by weight; component (e) is from about 0.01 to about 5% of the composition by weight; component (f) is from about 0.5 to about 5% of the composition by weight; and component (g) is from about 0.01 to about 5% of the composition by weight.

3. The composition of claim 1 wherein component (c) comprises a methylated soybean oil.

4. The composition of claim 1 wherein the at least one biologically active agent other than the at least one carboxamide arthropodicide is selected from abamectin, acetamiprid, amitraz, avermectin, azadirachtin, bifenthrin, buprofezin, cartap, chlorfenapyr, chlorpyrifos, clothianidin, cyfluthrin, beta-cyfluthrin, cyhalothrin, lambda-cyhalothrin, cypermethrin, cyromazine, deltamethrin, dieldrin, dinotefuran, diofenolan, emamectin, endosulfan, esfenvalerate, ethiprole, fenothiocarb, fenoxycarb, fenvalerate, fipronil, flonicamid, flufenoxuron, hexaflumuron, hydramethylnon, imidacloprid, indoxacarb, lufenuron, metaflumizone, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, tebufenozide, thiacloprid, thiamethoxam, thiodicarb, thiosultap-sodium, tralomethrin, triazamate, triflumuron, *Bacillus thuringiensis* subsp. *aizawai*, *Bacillus thuringiensis* subsp. *kurstaki*, nucleopolyhedrovirus, and an encapsulated delta-endotoxin of *Bacillus thuringiensis*.

5. A method for controlling an arthropod pest, comprising diluting a arthropodicidal suspension concentrate composition of claim 1 with water, and optionally adding an adjuvant to form a diluted composition, and contacting the arthropod pest or its environment with an effective amount of said diluted composition.

* * * * *